(12) United States Patent
Ploug et al.

(10) Patent No.: US 7,026,282 B1
(45) Date of Patent: Apr. 11, 2006

(54) PEPTIDE ANTAGONISTS OF THE HUMAN UROKINASE RECEPTOR AND METHOD FOR SELECTING THEM

(75) Inventors: Michael Ploug, Copenhagen (DK); Søren Østergaard, Copenhagen (DK); Claus Holst-Hansen, Frederiksberg (DK); Ross Stephens, Charlottenlund (DK); Keld Danø, Charlottenlund (DK); Arne Holm, Holte (DK)

(73) Assignee: Cancerforskningsfonden AF 1989 (Fonden Til Fremme AF Exsperimentel Cancerforskning), Copenhagen (DK)

( * ) Notice: Subject to any disclaimer, the term of this patent is extended or adjusted under 35 U.S.C. 154(b) by 0 days.

(21) Appl. No.: 09/743,329

(22) PCT Filed: Jul. 1, 1999

(86) PCT No.: PCT/DK99/00377

§ 371 (c)(1),
(2), (4) Date: Dec. 26, 2001

(87) PCT Pub. No.: WO00/01802

PCT Pub. Date: Jan. 13, 2000

(30) Foreign Application Priority Data

Jul. 1, 1998  (DK) .......................... PA 1998 00874

(51) Int. Cl.
*C07K 7/00* (2006.01)
*C07K 7/06* (2006.01)

(52) U.S. Cl. ............................ 514/2; 514/15; 530/328; 530/350

(58) Field of Classification Search ................... 514/2, 514/15; 530/328
See application file for complete search history.

(56) References Cited

U.S. PATENT DOCUMENTS 5,256,657 A    10/1993   Singh et al.

FOREIGN PATENT DOCUMENTS

| WO | 9705257 | 2/1997 |
| WO | 9724453 | 7/1997 |
| WO | 9735969 | 10/1997 |
| WO | 9737020 | 10/1997 |

OTHER PUBLICATIONS

Jain, Rakesh, Delivery of Molecular Medicine to Solid Tumors, Science, vol. 271, p 1079-1080, Feb. 1996.*
Dermer, Gerald. Anotehr Anniversary for the War on Cancer', Bio/Technolgoy, vol. 12, Mar. 1994.*
Gura, Trisha. Systems for Identifying New Drugs are Often Faulty, Science, vol. 278, pp 1041-1042.*
Golden, Fredrick, Of Mice And Men: Don't Blame the Rodents, Time, pp. 44, May 18, 1998.*
Ngo et al., 'Computational Complexity, Potein Structure Prediction, and The Levinthal Paradox,' The Protein Folding Problem and Tertiary Structuer Prediction. Ed. K. Merz and L. Le Grand. BirkHauser, Boston MA. pp. 491-495. 1994.*
Rudinger, J. (1976), Peptide Hormones (ed. J.A. Parsons). University Park Press. Baltimore. pp 1-7.*
Burgle, et al., *Inhibition of the Interaction of Urokinase-Type Plasminogen Activator (uPA) with Its Receptor (uPAR) by Synthetic Peptides,* Biol. Chem., vol. 378, pp. 231-237, Mar./Apr. 1997.
Fauchere, et al., *Amino acid side chain parameters of correlation studies in biology and pharmacology,* International Journal of Peptide and Protein Research, vol. 32, No. 4, pp. 269-278, Oct. 4, 1998.
Goodson, et al., *High-affinity urokinase receptor antagonists identified with bacteriophage peptide display,* Proc. Natl. Sci. USA , vol. 91, pp. 7129-7133, Jul., 1994.
Holst-Hansen, *The Human Urokinase Receptor in Tumor Xenografted Mice: A Plasma Parameter of Tumor Burden and a Target of Anti-Tumor Therapy,* The Finsen Laboratory, Rigshospitalet, Ph.D Thesis, The Medical Faculty, University of Copenhagen, Denmark, pp. 1-128, Jun. 1998.
Luther, et al., *Epitope-Mapped Monoclonal Antibodies as Tools for Functional and morphological Analyses of the Human Urokinase Receptor in Tumor Tissue,* American Journal of Pathology, vol. 150, pp. 1231-1244, Apr. 1997.

(Continued)

*Primary Examiner*—Anish Gupta
(74) *Attorney, Agent, or Firm*—Iver P. Cooper

(57) ABSTRACT

A novel set of inhibitors of the binding interaction between human urokinase plasminogen activator (uPA) and its cell surface receptor (uPAR) has been developed. The inhibitors comprise of peptide fragments, monomeric or in multiple copies attached to a common scaffold, in which the amino acid sequence may include uncommon substituted amino acids to partially comprise of peptoid sequences. The present invention also relates to the use of such peptides in therapy, in particular for the treatment of cancer, having developed a modified non-human mammalian receptor to which the novel inhibitors are antagonistic.

35 Claims, 10 Drawing Sheets

OTHER PUBLICATIONS

Min, et al., *Urokinase Receptor Antagonists Inhibit Angiogenesis and Primary Tumor Growth in Syngeneic Mice*, Cancer Research, vol. 56, pp. 2428-2433, May 15, 1996.

Ploug, et al., *Photoaffinity Labeling of the Human Receptor for Urokinase-Type Plasminogen Activator Using a Decapeptide Antagonist. Evidence for a Composite Ligand-Binding Site and a Short Interdomain Separation*, Biochemistry, vol. 37, pp. 3612-3622, 1998.

Ploug, et al., *Glycosylation Profile of a Recombinant Urokinase-type Plasminogen Activator Receptor Expressed in Chinese Hamster Ovary cells*, The Journal of Biological Chemistry, vol. 273, pp. 13933-13943, 1998.

* cited by examiner

Figure 9

|  | uPAR domain I loop 3 | uPAR domain III loop 3 | % identity |
|---|---|---|---|
| huPA/antagonist | * * * * | → | |
| Human (+/+) | WHEKTNRT L SYRTLKITSLT E VV | Q H HLD F SMNHIDVS | (100) |
| Hamster (+/−) | WHEKTNRT M SYRVSKIISLA E VV | QG HVD F LLSHPNIS | (63.5) |
| Mouse (−/−) | WHEKTNRT M SYRMSMIISLT E TV | QG HVD F PTHNVSVS | (62.2) |
| Rat (−/?) | WHEKTNRT M SYRMSVIVSLT E TV | QG HVD F QTHNLSTS | (62.5) |
| Bovine (?/?) | WHDKTNRS M SYRADQIITLS E TV | QS HVE F DLTHVNVS | (61.6) |

PEPTIDE ANTAGONISTS OF THE HUMAN UROKINASE RECEPTOR AND METHOD FOR SELECTING THEM

FIELD OF THE INVENTION

The present invention relates to novel peptide inhibitors of the binding interaction between human urokinase plasminogen activator (in the following referred to as uPA) and its cell surface receptor (in the following referred to as uPAR). The present invention also relates to such peptides for use in therapy.

GENERAL BACKGROUND

The use of inhibitors of the binding interaction between uPA and uPAR provide a method for preventing or counteracting localised extracellular proteolytic activity in a mammal, in particular a human, by preventing the binding of a receptor-binding form of uPA to uPAR in the mammal and thereby reducing the ability of uPA to convert plasminogen into plasmin. This mechanism is inter alia described in N. Behrendt et al. (1995) *Biol. Chem. Hoppe-Seyler*, 376: 269–279 and in WO 90/12091. While the binding of uPA is known to be necessary for optimal performance of cell-surface proteolysis, blocking of uPA may also have other anti-tumour effects in the context of cell signalling, cell adhesion and migration. Such alternative mechanisms are e.g. suggested in Min et al., Cancer Research, 56: 2428–2433 (1996).

Peptide inhibitors of the uPA/uPAR interaction have previously been described (see R. J. Goodson et al. (1994) *Proc. Nat. Acad. Sci. U.S.A.* 91:7129–7133; M. Bürgle et al. (1997) *Biol. Chem.* 378: 231–237; U.S. Pat. No. 5,656,726; WO 97/35969 and WO 97/24453).

Thus, Goodson et al. disclosed nineteen linear 15-mers comprising of two relatively short conserved subsequences: LWXXAr (Ar=Y, W, F or H) and XFXXYLW, neither of which are found in uPA or its receptor (uPAR). The peptides were tested in a UPAR binding assay, wherein the most potent inhibitor (the so-called "Clone 20": AEPMPHSLN-FSQYLWYT (SEQ ID NO:2)) showed an apparent inhibition constant at 10 nM for the uPAR-ATF interaction.

Bürgle, et al. studied the ability of synthetic peptides derived from the uPAR binding region of uPA (i.e. comprising the amino acids 16–32 of uPA) to inhibit the uPA/uPAR interaction. Moreover, various disulfide-bridged cyclic forms of the above-mentioned peptide were tested and it was found that the cyclo$^{19,31}$uPA$_{19-31}$ was a relatively potent inhibitor of the uPA/uPAR interaction.

WO 97/35969 (Chiron) describes a number of peptides capable of binding to uPAR thereby inhibiting the binding of an integrin and vitronectin.

WO 97/05257 (Chiron) relates inter alia to polypeptides and analogues thereof capable of binding to uPAR and thereby inhibit the receptor binding activity of uPA. The peptides studied all comprised the following sequence:

L-(N/C)F-(G/s)-(Q/C/c)-Y-L-(W/nA)-(Y/C)-T wherein capital letters designate L-amino acids, lower case letters designate D-amino acids and nA denotes 1-naphthylalanine. It was found that inclusion of D-serine in the position next to the fixed phenylalanine in most cases caused a 2–5 fold decrease in the obtained IC$_{50}$ value.

SUMMARY OF THE INVENTION

The present invention provides peptides having considerably higher affinity for uPAR, lower off-rates, high potency in a cell-binding system, and demonstrated biological stability.

Thus, in a first aspect the present invention relates to a peptide comprising at least one peptide fragment of the general formula I:

$$-X_1-X_2-X_3-X_4-X_5-X_6-X_7-X_8-X_9- \quad (1)$$

wherein
$X_1$, $X_5$, $X_6$, $X_7$ and $X_9$ are independently selected from amino acids and $X^1$ is the N-terminal amino acid of the fragment and $X^9$ is the C-terminal amino acid of the fragment;

$X^2$ is selected from the group consisting of amino acids of the general formula IIa $$-NH-\underset{R^2}{\underset{|}{\overset{\overset{R^1}{|}}{\overset{|}{\underset{|}{C}}}}}-C(=O)- \quad (IIa)$$

$$\text{with } (CH_2)_n \text{ on } C$$

wherein n is an integer in the range from 0 to 3; $R^1$ is selected from the group consisting of optionally substituted five-, six- and seven-membered non-aromatic rings; $R^2$ is selected from the group consisting of hydrogen and $C_{1-4}$-alkyl; or, $R^1$ and $R^2$ together with the carbon atom to which they are bound form an optionally substituted cyclopentyl, cyclohexyl, cycloheptyl or decahydronaphthalenyl ring; and N-substituted amino acids of the general formula IIb $$-N-CH_2-C(=O)- \quad (IIb)$$

$$\text{with } (CH_2)_n \text{ and } R^1 \text{ on } N$$

wherein n and $R^1$ are as defined above.

$X^3$ and $X^8$ are each independently selected from the group consisting of amino acids having hydrophobic side chains and amino acids having hydrophobic N-substituents;

$X^4$ is selected from the group consisting of amino acids of the general formula IIIa $$-NH-\underset{H}{\underset{|}{\overset{\overset{Y}{|}}{\overset{|}{\underset{|}{C}}}}}-C(=O)- \quad (IIIa)$$

$$\text{with } (CH_2)_m \text{ on } C$$

wherein m is an integer in the range from 1 to 3, and Y is selected from the group consisting of OH, SH, NH$_2$, CONH$_2$, COOH and OPO$_3$H; and N-substituted amino acids of the general formula IIIb

wherein m and Y are as defined above;

Moreover the present invention relates to in vitro and in vivo methods for selecting peptide antagonists which are suitable for preventing or counteracting localized extracellular proteolytic activity of plasmin in a human.

In further aspects the present invention relates to a peptide as defined above for use as a medicament, to the use of the peptide defined above for the manufacture of a medicament for treatment of cancer, and to a pharmaceutical composition comprising the peptide of the invention.

DETAILED DESCRIPTION OF THE INVENTION

In the present context the term "$C_{1-7}$-alkyl" used alone or as part of another group designates a linear, branched or cyclic saturated hydrocarbon group having from one to seven carbon atoms, such as methyl, ethyl, n-propyl, isopropyl, n-butyl, isobutyl, sec-butyl, tert-butyl, cyclobutyl, pentyl, isopentyl, neopentyl, cyclopentyl, hexyl, cyclohexyl, heptyl and cycloheptyl. Analogously, the term "$C_{1-4}$-alkyl" used alone or as part of another group designates a linear, branched saturated hydrocarbon group having from one to four carbon atoms, such as methyl, ethyl, n-propyl, isopropyl, n-butyl, isobutyl, sec-butyl and tert-butyl.

In the present context the term "$C_{2-8}$-alkenyl" is intended to mean a linear, branched or cyclic hydrocarbon group having from two to eight carbon atoms and containing one or more double bonds. Examples of $C_{2-8}$-alkenyl groups include olefins such as allyl, homo-allyl, vinyl, crotyl, butenyl, pentenyl, hexenyl, heptenyl and octenyl. Examples of $C_{2-8}$-alkenyl groups with more than one double bond include butadienyl, pentadienyl, hexadienyl, heptadienyl, hexatrienyl, heptatrienyl and octatrienyl groups as well as branched forms of these. Preferred examples of $C_{2-8}$-aklenyls are vinyl, allyl and butenyl.

In the present context the term "$C_{2-8}$-alkynyl" is intended to mean linear, branched or cyclic hydrocarbon groups containing from two to eight carbon atoms and containing one or more triple bonds. Examples of $C_{2-8}$-alkynyl groups include acetylene, propynyl, butynyl, pentynyl, hexynyl, heptynyl and octynyl groups as well as branched forms of these.

When used herein the term "$C_{2-8}$-alkoxy" is intended to mean $C_{1-7}$-alkyl-oxy such as methoxy, ethoxy, n-propoxy, isopropoxy, n-butoxy, isobutoxy, sec-butoxy, tert-butoxy, pentoxy, isopentoxy, neopentoxy, hexoxy and heptoxy. In a similar way, when used herein the term "$C_{1-4}$-alkoxyl" is intended to mean $C_{1-4}$-alkyl-oxy such as methoxy, ethoxy, n-propoxy, isopropoxy, n-butoxy, isobutoxy, sec-butoxy and tert-butoxy.

In the present context the term "aryl" used alone or as part of another group is intended to mean an aromatic carbocyclic ring or ring system, such as phenyl, naphthyl, anthracyl, phenanthracyl, pyrenyl, benzopyrenyl, fluorenyl, and xanthenyl, preferably phenyl.

The term "heteroaryl" is intended to mean an aryl group where one or more carbon atoms have been replaced with heteroatoms such as nitrogen, sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrazinyl, pyridazinyl, piperidinyl, coumaryl, furyl, quinolyl, indolyl, benzopyrazolyl, and phenoxazonyl.

In the present context the term "five-, six- and seven-membered non-aromatic ring" is intended to cover five-, six- and seven-membered rings comprising carbon atoms only (carbocyclic) or carbon atoms together with from 1 to 3 heteroatoms (heterocyclic), wherein the heteroatoms are independently selected from oxygen, sulphur, and nitrogen. Such rings may contain no unsaturated bonds or may contain one or more unsaturated bonds, however, if present, situated in such a way that an aromatic π-electron system does not arise.

Examples of preferred "five-, six- and seven-membered non-aromatic rings" are cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene, 1,3,5 cycloheptatriene, 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1, 2-thiazine, 2H-1,3-thiazine, 4H-1,3-thiazine, 5,6-dihydro-4H-thiazine, 4H-1,4-thiazine, tetrahydro-1,4-thiazine, 2H-1, 2-oxazine, 4H-1,2-oxazine, 6H-1,2-oxazine, 2H1,3-oxazine, 4H-1,3-oxazine, 4H-1,4-oxazine, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane, 1,2,4-trioxolane, 1,2,3-triazoline and 1,2,3-triazolidine.

The term "halogen" includes fluorine, chlorine, bromine and iodine.

In the present context, i.e. in connection with the terms "aryl", "heteroaryl", "carbocyclic", "cyclopentyl", "cyclohexyl", "cycloheptyl", "decahydronaphthalenyl", "five-, six- and seven-membered non-aromatic ring", "$C_{1-7}$-alkyl", "$C_{1-7}$alkoxy", "$C_{2-8}$-alkenyl", and "$C_{2-8}$-alkynyl", the term "optionally substituted" is intended to mean that the group in question may be substituted one or several times, such as 1 to 5 times, preferably 1 to 3 times, with one or more groups selected from $C_{1-7}$-alkyl, such as $C_{1-4}$-alkyl, $C_{1-7}$alkoxy, such as $C_{1-4}$-alkoxy, oxo (which may be represented in the tautomeric enol form), carboxy, amino, hydroxy (which when present in an enol system may be represented in the tautomeric keto form), nitro, sulphono, sulphanyl, $C_{1-7}$-carboxy, $C_{1-7}$-alkoxycarbonyl, $C_{1-7}$-alkylcarbonyl, formyl, aryl, aryloxy, aryloxycarbonyl, arylcarbonyl, heteroaryl, amino, mono- and di($C_{1-7}$-alkyl)amino; carbamoyl, mono- and di($C_{1-7}$-alkyl)aminocarbonyl, amino-$C_{1-7}$-alkyl-aminocarbonyl, mono- and di($C_{1-7}$-alkyl)amino-$C_{1-7}$-alkyl-aminocarbonyl, $C_{1-7}$-alkylcarbonylamino, cyano, guanidino, carbamido, $C_{1-7}$-alkanoyloxy, sulphono, $C_{1-7}$-alkylsulphonyloxy, nitro, sulphanyl, dihalogen-$C_{1-4}$-alkyl, trihalogen-$C_{1-4}$-alkyl, halogen, where aryl and heteroaryl representing substituents may be substituted 1–3 times with $C_{1-4}$-alkyl, $C_{1-4}$-alkoxy, nitro, cyano, hydroxy, amino or halogen. Preferred examples are hydroxy, $C_{1-4}$-alkyl, $C_{1-4}$-alkoxy, carboxy, $C_{1-4}$-alkoxycarbonyl, $C_{1-4}$-alkylcarbonyl, aryl, amino, mono- and di($C_{1-4}$alkyl)amino, and halogen, wherein aryl may be substituted 1–3 times with $C_{1-4}$-alkyl, $C_{1-45}$ alkoxy, nitro, cyano, amino or halogen.

In the present context the term "amino acid", unless otherwise stated, is intended to cover the common α-amino acids, i.e., L-alanine (A), L-valine (V), L-leucine (L), L-isoleucine (I), L-methionine (M), L-phenylalanine (F), L-tryptophan (W), L-proline (P), glycine (G), L-serine (S), L-threonine (T), L-cysteine (C), L-tyrosine (Y), L-asparagine (N), L-glutamine (Q), L-lysine (K), L-arginine (R), L-histidine (H), L-aspartic acid (D) and L-glutamic acid (E).

The term "amino acid", however, is also intended to cover unconventional α-amino acids such as D-amino acids, α-alkylated amino acids, such as α-methylated amino acids and N-substituted amino acids, in particular N-substituted glycines.

Examples of such unconventional amino acids are D-alanine (a), D-valine (v), D-leucine (l), D-isoleucine (i), D-methionine (m), D-phenylalanine (f), D-tryptophan (w), D-proline (p), D-serine (s), D-threonine (t), D-cysteine (c), D-tyrosine (y), D-asparagine (n), D-glutamine (q), D-lysine (k), D-arginine (r), D-histidine (h), D-aspartic acid (d), D-glutamic acid (e), L-norleucine, L-homophenylalanine, D-ornithine, L-ethylglycine, penicillamine, cyclohexyl-alanine, 1-aminocyclopropane-1-carboxylate, L-α-methylalanine, L-α-methylaspartic acid, L-α-methylphenylalanine, L-α-isoleucine, L-α-methylleucine, L-α-methylasparagine, L-α-methylglutamine, L-α-methylserine, L-α-methylvaline, L-α-methylnorleucine, L-α-methyl-norvaline, L-α-methylethylglycine, α-methylaminoisobutyric acid, α-methylpenicillamine, α-methylcyclohexylalanine, D-α-methylalanine, D-α-methylcysteine, D-α-methylglutamic acid, α-amino butyic acid, L-norvaline, α-aminoisobutyric acid, L-α-t-butylglycine, α-naphthylalanine, cyclopentylalanine, 1-aminonorbornyl-1-carboxylate, L-α-methylcysteine, L-α-methylglutamic acid, L-α-methylhistidine, L-α-methyllysine, L-α-methylmethionine, L-α-methylproline, L-α-methylarginine, L-α-methylthreonine, L-α-methyltryptophan, L-α-methylornithine, α-amino-α-methylbutyric acid, L-α-methylhomophenylalanine, L-α-methyl-t-butylglycine, α-methyl-α-naphthylalanine, α-methylcyclopentylalanine, D-α-methylaspartic acid, D-α-methylphenylalanine, D-α-methylhistidine, D-α-methyllysine, D-α-methylmethionine, D-α-methylproline, D-α-methylarginine, D-α-methylthreonine, D-α-methyltryptophan, D-α-methylisoleucine, D-α-methylleucine, D-α-methylasparagine, D-α-methylglutamine, D-α-methylserine, D-α-methylvaline, D-α-methyltyrosine, L-N-methylalanine, L-N-methylphenylalanine, L-N-methylisoleucine, L-N-methylleucine, L-N-methylasparagine, L-N-methylglutamine, L-N-methylserine, L-N-methylvaline, L-N-methyltyrosine, L-N-methylnorleucine, L-N-methylnorvaline, N-methylcyclopentylalanine, N-methylpenicillamine, N-methylaminoisobutyric acid, D-N-methylalanine, D-N-methylcysteine, D-N-methylglutamic acid, D-N-methylhistidine, D-N-methyllysine, D-N-methylmethionine, D-N-methylproline, D-N-methylarginine, D-N-methylthreonine, D-N-methyltryptophan, N-methylglycine (sarcosine), L-N-methylcysteine, L-N-methylglutamic acid, L-N-methylhistidine, L-N-methyllysine, L-N-methylmethionine, N-methylcyclohexy-alanine, L-N-methylarginine, L-N-methylthreonine, L-N-methyltryptophan, L-N-methylornithine, N-amino-α-methylbutyric acid, L-N-methylhomophenylalanine, N-methyl-α-naphthylaianine, D-N-methylornithine, D-N-methylaspartic acid, D-N-methylphenylalanine, D-N-methylisoleucine, D-N-methylleucine, D-N-methylasparagine, D-N-methylglutamine, D-N-methylglutamine, D-N-methylserine, D-N-methylvaline, D-N-methyltyrosine, and N-substituted glycines such as, e.g., L-N-methylethylglycine, N-(2-carboxyethyl)glycine, N-(imidazolylethyl)glycine, N-(4-aminobutyl)glycine, N-(2-methylthioethyl)glycine, N-(carbamylmethyl)glycine, N-(1-methylethyl)glycine, L-N-methyl-tbutylglycine, N-(carboxymethyl)glycine, N-ethylglycine, N-benzylglycine, N-(120 methylpropyl)glycine, N-(2-methylpropyl)glycine, N-(hydroxyethyl)glycine, N-(2-carbamylethyl)glycine, N-(3-guanidinopropyl)glycine, N-(3-indolylethyl)glycine, N-(1-hydroxyethyl)glycine, N-(3-aminopropyl)glycine, N-cyclobutylglycine, N-cycloheptylglycine, N-cyclodecylglycine, N-cyclododecylglycine, N-(3,3-diphenylpropyl)glycine, N-(N-(2,2-diphenylethyl)carbamylmethyl)glycine), N-(N-(3,3-diphenylpropyl)carbamylmethyl)glycine), N-(2-(4-methoxy)-phenyl)glycine, 1-carboxy-1-(2,2-diphenylethylamino)cyclopropane, N-(2-aminoethyl)glycine, N-(p-hydroxyphenethyl)glycine, N-(thiomethyl)glycine, N-cyclopropylglycine, N-cyclohexylglycine, N-methylcyclohexylglycine, N-cyclooctylglycine, N-cycloundecylglycine and N-(2,2-diphenylethyl)glycine, N-(2,3-dimethoxybenzyl)glycine, N-(naphthyl)glycine, N-(methylnaphthalyl)glycine, N-(indanyl)-glycine, N-(diphenylethyl)glycine and N-(2-methoxyethyl)glycine.

Thus, in the present context the term "substituted" as part of the terms "N-substituted glycines" and "N-substituted amino acids" is intended to mean the case where an amine hydrogen is replaced by a hydrocarbon group such as optionally substituted $C_{1-7}$-alkyl, optionally substituted $C_{2-8}$-alkenyl, and optionally substituted $C_{2-8}$-alkynyl groups. The term "substituent" refers to the group that has replaced the hydrogen on the amine nitrogen. Analogously, the term "side chain", when used herein, refers to the actual substituent (or substituents) on the α-carbon atom. Thus, the term "side chain" does not refer to substituents present on the amine nitrogen atom of the amino acid, cf. above.

Thus, the amino acids $X^1$, $X^5$, $X^6$, $X^7$ and $X^9$ in the peptide fragment of the general formula I, as defined above, are independently selected from such amino acids as mentioned above. Preferably, however, the, amino acids $X^1$, $X^5$, $X^6$, $X^7$ and $X^9$ are independently selected from the group consisting of L-alanine, L-valine, L-leucine, L-isoleucine, L-methionine, L-phenylalanine, L-tryptophan, L-proline, glycine, L-serine, L-threonine, L-cysteine, L-tyrosine, L-asparagine, L-glutamine, L-lysine, L-arginine, L-histidine, L-aspartic acid, L-glutamic acid, D-alanine, D-valine, D-leucine, D-isoleucine, D-methionine, D-phenylalanine, D-tryptophan, D-proline, D-serine, D-threonine, D-cysteine, D-tyrosine, D-asparagine, D-glutamine, D-lysine, D-arginine, D-histidine, D-aspartic acid and D-glutamic acid as well as the N-substituted glycine analogues of the above-mentioned amino acids. Thus, as will be understood by the person skilled in the art, the term "N-substituted glycine analogues" means that the N-substituent on the N-substituted glycine is similar (and, in some cases identical) to the side chain of the amino acid in question. This may be further illustrated by the following example; The "N-substituted glycine analogue" to alanine is N-methyl-glycine as the methyl group has been "transposed" from the α-carbon to the amine part of the molecule. Accordingly, the amino acid alanine may be considered as an α-methyl substituted glycine molecule.

As will be apparent from the examples provided herein, the amino acid $X^2$ in the peptide fragment of the general formula I, as defined above, is of utmost importance for efficient binding of the peptides of the invention to the uPAR. Without being limited thereto, it is presently believed that some aliphatic ring system must be present at the side chain of the $X^2$ amino acid (or, in an analogous way, some aliphatic ring system must be present on the N-substituent of the N-substituted $X^2$ amino acid) in order to enhance the binding of the peptide to uPAR.

Thus, in one interesting embodiment of the invention $X^2$ is an amino acid of the general formula IIa

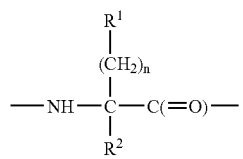

(IIa)

wherein n is an integer in the range from 0 to 3, such as 1, 2 or 3, preferably 1 or 2. $R^1$ is selected from the group consisting of optionally substituted five-, six- and seven-membered non-aromatic rings such as cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene, 1,3,5 cycloheptatriene, 2H-thipyran, 3H-thipyran, 4H-thipyran, tetrahydrothiopyran, 2H-pyran, 4H-pyran, tetrahydropyran, piperidine, 1,2-dithiin, 1,2-dithiane, 1,3-dithiin, 1,3-dithiane, 1,4-dithiin, 1,4-dithiane, 1,2-dioxin, 1,2-dioxane, 1,3-dioxin, 1,3-dioxane, 1,4-dioxin, 1,4-dioxane, piperazine, 1,2-oxathiin, 1,2-oxathiane, 4H-1,3-oxathiin, 1,3-oxathiane, 1,4-oxathiin, 1,4-oxathiane, 2H-1,2-thiazine, tetrahydro-1,2-thiazine, 2H-1,3-thiazine, 4H-1,3-thiazine, 5,6-dihydro-4H-thiazine, 4H-1,4-thiazine, tetrahydro-1,4-thiazine, 2H-1,2-oxazine, 4H-1,2-oxazine, 6H-1,2-oxazine, 2H-1,3-oxazine, 4H-1,3-oxazine, 4H-1,4-oxazine, morpholine, trioxane, 4H-1,2,3-trithiin, 1,2,3-trithiane, 1,3,5-trithiane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,2-dioxole, 1,2-dioxolane, 1,3-dioxole, 1,3-dioxolane, 3H-1,2-dithiole, 1,2-dithiolane, 1,3-dithiole, 1,3-dithiolane, isoxazoline, isoxazolidine, oxazoline, oxazolidine, thiazoline, thiozolidine, 3H-1,2-oxathiole, 1,2-oxathiolane, 5H-1,2-oxathiole, 1,3-oxathiole, 1,3-oxathiolane, 1,2,3-trithiole, 1,2,3-trithiolane, 1,2,4-trithiolane, 1,2,3-trioxole, 1,2,3-trioxolane, 1,2,4-trioxolane, 1,2,3-triazoline and 1,2,3-triazolidine.

$R^2$ is hydrogen or $C_{1-4}$-alkyl, such as methyl or ethyl, but preferably hydrogen.

As indicated above, $X^2$ may be an amino acid of the general formula IIa. However, in a preferred embodiment of the invention, the $X^2$ amino acid is restricted to a specific stereochemistry around the asymmetric α-carbon atom. Therefore, $X^2$ preferably has the structure as indicated in the general formula IIc:

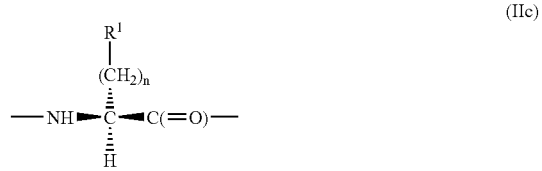

(IIc)

wherein n is 1 or 2 and $R^1$ is as defined above.

In a particular interesting embodiment of the invention $R^1$ is cyclopentyl, cyclohexyl or cycloheptyl and n is preferably 1, i.e. specific examples of amino acids which are especially suitable in the $X^2$ position are β-cyclopentyl-L-alanine, β-cyclohexyl-L-alanine and β-cycloheptyl-L-alanine, in particular β-cyclohexyl-L-alanine.

In another interesting embodiment of the invention, $R^1$ and $R^2$ together with the α-carbon atom to which they are attached form an optionally substituted carbocyclic ring, preferably a cyclopentyl, cyclohexyl or cycloheptyl ring. Furthermore, $R^1$ and $R^2$ together with the α-carbon atom to which they are attached may form a decahydronaphthalenyl ring. It should be understood that the decahydronaphthalenyl ring, when attached to the amino acid skeleton, may appear in several different isomeric forms (vide infra). First of all, when the decahydronaphthalenyl group is formed together with the α-carbon atom of the $X^2$ amino acid, two different structural isomers are possible (vide infra). In addition to that, each of the structural isomers may exist in four different diastereomeric forms as well as the mirror images thereof. Thus, the decahydronaphthalenyl ring, when attached to the amino acid skeleton, may appear in a total of sixteen different isomeric forms which are all within the scope of the invention. In other words, in an interesting embodiment of the invention, the amino acid $X^2$ has the following structures:

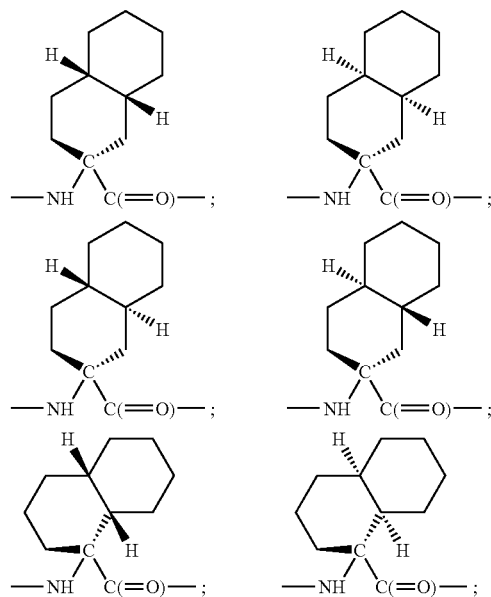

-continued

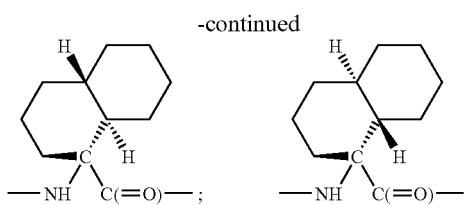

as well as the mirror image stereoisomers thereof.

As mentioned above, and as will be understood from the examples provided herein, α-cyclohexyl-L-alanine is especially suitable as the $X^2$ amino acid. Accordingly, although a total of sixteen different isomers are possible for the decahydronaphthalenyl ring system, it is envisaged that the following structures (as well as the mirror images thereof) are particular suitable as the $X^2$ amino acid since these structures resemble the β-cyclohexylalanine structure:

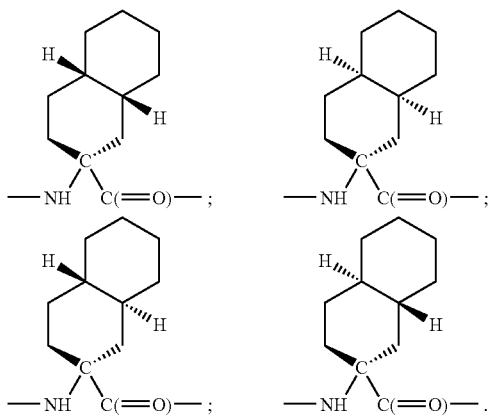

The structures shown above (as well as the mirror images thereof) may be considered as being β-cyclohexylalanine analogues, wherein the cyclohexyl ring of β-cyclohexylalanine has been "locked" in specific conformations.

In a further interesting embodiment of the invention $X^2$ is an N-substituted amino acid (or, more precisely, an N-substituted glycine) of the general formula IIb

(IIb)

wherein $R^1$ and n are as defined above.

As will be understood from the examples provided herein, in several cases similar performance by the peptide is achieved whether the side chain is present on the α-carbon atom or present as an N-substitutent on the amine group of the N-substituted glycine. Thus, in this interesting embodiment of the invention $R^1$ and n, when used in connection with formula IIb above, are preferably the same as discussed in connection with formula IIa and IIc above, i.e. n is preferably 1 or 2, in particular 1 and $R^1$ is preferably selected from the group consisting of cyclopentyl, cyclohexyl and cycloheptyl, in particular cyclohexyl.

As it appears from the examples provided herein, in the $X^3$ and $X^8$ positions, amino acids having a hydrophobic side chain or a hydrophobic N-substituent seem to enhance the binding properties of the peptide to the receptor, which could be due to hydrophobic interactions between the side chains or N-substituents of the $X^3$ and $X^8$ amino acids and hydrophobic residues in the uPAR binding region. Thus, $X^3$ and $X^8$ are preferably selected from amino acids with side chains or N-substituents with a hydrophobicity constant (π) of at least 0.5.

The hydrophobicity constant (π) expresses the hydrophobicity of the side chain or N-substituent relative to the hydrogen atom (or, in other words: The hydrophobicity constant (π) expresses the hydrophobicity of the acetylated amino acid amide in question relative to acetylglycine amide).

In the present context, the hydrophobicity constant (π) is defined as described in J. L. Fauchere et al. (1988) *Int. J. Peptide Protein Res.* 32:269–278:

$$\pi = \log P_{(Ac\text{-}amino\ acid\text{-}NH2)} - \log P_{(Ac\text{-}Gly\text{-}NH2)} \quad (Q)$$

wherein P is the partition coefficient of the acetylated amino acid amide in the water-octanol system.

Expression Q is an application of the Hansch equation (S) (C. Hansch et al. (1964), *J. Am. Chem. Soc.* 86: 5175, Hansch et al. (1971) *Chem Rev.* 71: 525) to amino acids:

$$\pi = (\log P)/(\log P_0) \quad (S)$$

wherein P is the partition coefficient of the substituted compound and $P_0$ is the partition coefficient of the parent compound in the water-octanol system.

Thus, the hydrophobicity of any given amino acid may readily be expressed by the above-defined π-value. π-values for a number of amino acid side chains can be found in e.g. J. L Fauchére et al. (1988) *Int. J. Peptide Protein Res.* 32:269–278, or, as an alternative, the π-value of the amino acid in question can be calculated in accordance with formula Q defined above, using the water-octanol partition constant (P) for the corresponding acetylated amino acid amide. The water-octanol partition constant (P) may be determined by methods known in the art, e.g. such as described in V. Pliska et al. (1981) *J. Chromatogr.* 216: 79–92.

As discussed above, formula Q typically relates to the hydrophobicity constant (π) of the side chain of an amino acid relative to hydrogen. However, since formula Q is merely an extension of the Hansch equation (S) specifically to amino acids, it is easily applicable to N-substituted amino acids given that in this circumstance, the term also relates to the hydrophobicity of a group relative to that of hydrogen. Thus, the partition coefficient of N-substituted glycines can be compared to that of glycine (once derivatised to their corresponding acetylated glycine amides), as can the partition coefficient of any N-substituted amino acid since the original Hansch equation (S) relates to the additive contribution to the hydrophobicity constant by a substituent relative to that of the hydrogencontaining parent compound.

As it appears from the formula Q, defined above, the hydrophobicity constant (π) of glycine is zero as the π-value of the amino acid side chain is measured relative to the hydrogen atom.

In preferred embodiments of the invention, the side chains or N-substituents of the $X^3$ and $X^8$ amino acids have a hydrophobicity constant (π), as defined above, of at least 0.75, preferably at least 1.0, such as at least 1.5, e.g. at least 2.0, or even as high as at least 2.5.

Specific examples of suitable amino acids to be incorporated in the $X^3$ and $x^8$ positions are e.g. aromatic L- and D-amino acids, such as D- and L-phenylalanine, D- and L-tryptophan, D- and L-tyrosine, D- and L-histidine, β-2-naphthyl-L-alanine, β-2-naphthyl-D-alanine, β-1-naphthyl-L-alanine, β-1-naphthyl-D-alanine as well as aromatic N-substituted glycines, such as N-(2,3-dimethoxybenzyl) glycine, N-(3-indolylethyl)glycine, N-benzylglycine, N-(methylnaphthalyl)glycine, N-(2,2-diphenylethyl)glycine, N-(indanyl)glycine, N-(2-ethyl-2-pyridinyl)glycine, N-(4-methoxyphenylethyl)glycine. Examples of amino acids which are especially suitable for incorporation in the $X^3$ and $X^8$ position, respectively, are L-phenylalanine in the $X^3$ position, and L-tryptophan, N-benzylglycine, N-(methylnaphthalyl)glycine or N-(2,3-dimethoxybenzyl)glycine in the $X^8$ position.

In an interesting embodiment of the invention the amino acid $X^4$ is selected from L- and D-amino acids of the general formula IIIa

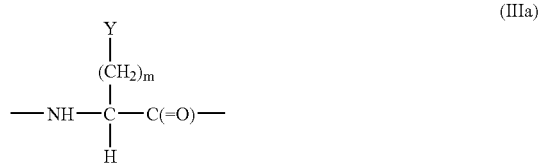

wherein m is an integer in the range from 1 to 3, such as 1, 2 or 3, and Y is a group capable of donating and/or accepting one or more hydrogen bonds such as OH, SH, $NH_2$, $CONH_2$, COOH and $OPO_3H$.

Specific amino acids of the general formula IIIa which are considered to be especially suitable for incorporation in the $X^4$ position are L-serine, D-serine, L-cysteine and D-cysteine, in particular D-serine.

Furthermore, it is envisaged that N-substituted glycines may also be suitable as the $X^4$ amino acid. Thus, in another interesting embodiment of the invention $X^4$ is selected from N-substituted amino acids of the below formula IIIb:

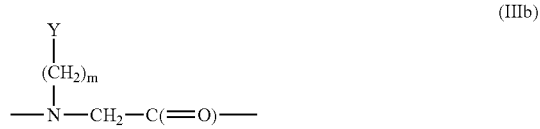

wherein m and Y are as defined above, i.e. m is preferably 1 or 2, in particular 1, and Y is group capable of donating and/or accepting one or more hydrogen bonds such as OH, SH, $NH_2$, $CONH_2$, COOH and $OPO_3H$, in particular OH and SH. Thus specific examples of N-substituted amino acids which are envisaged to be suitable $X^4$-amino acids are, for example, N-(hydroxymethyl)glycine, N-(hydroxyethyl) glycine, N-(methylthiol)glycine and N-(ethylthiol)glycine.

The peptide of the invention, comprising the amino acid sequence as defined in formula I above, may of course consist of the peptide fragment $X^1$- . . . -$X^9$ exclusively, or the peptide may consist of two or more repeating units of the peptide fragment $X^1$- . . . -$X^9$.

In another interesting embodiment of the invention, the peptide has the general formula IV $$Y^N\text{-}X^1\text{-}X^2\text{-}X^3\text{-}X^4\text{-}X^5\text{-}X^6\text{-}X^7\text{-}X^8\text{-}X^9\text{-}Y^C \qquad \text{(IV)}$$

wherein $Y^N$ is an N-terminal group, $Y^C$ is a C-terminal group, and $X^1$- . . . -$X^9$ is the peptide fragment I as defined above.

The N-terminal group ($Y^N$) may be such groups which are readily attached to an N-terminal amino acid of a peptide such as $C_{1-4}$-alkyl, $C_{1-4}$-alkylcarbonyl such as acetyl, optionally substituted arylcarbonyl, and optionally substituted heteroarylcarbonyl. The N-terminal group, however, may also be hydrogen (i.e. the N-terminal of the peptide is the free amine of the first amino acid ($X^1$) of the peptide fragment) or a peptide radical having 1–7 amino acids.

In a similar way, the C-terminal group ($Y^C$) may be such groups which are readily attached to a C-terminal group of a peptide such as $C_{1-4}$-alkoxy, $C_{1-4}$-alkylamino, optionally substituted arylamino, and optionally substituted heteroarylamino. The C-terminal group ($Y^C$), however, may also be OH (i.e. the C-terminal of the peptide is the free carboxylic acid of the last amino acid ($X^9$) of the peptide fragment), $NH_2$ (i.e. the C-terminal of the peptide is the amide of the last amino acid ($X^9$) of the peptide fragment) or a peptide radical having 1–7 amino acids. In the latter case, the amino acids may be the amino acids defined above as well as protected variants thereof.

Another possible meaning for the group $Y^C$ is a-linker-(peptide having 1–7 amino acids) moiety, which may be used with the aim of protecting a peptide according to the present invention against proteolytic degradation. This principle where a pre-sequence is attached to the peptide via a linker, e.g. an α-hydroxy carboxylic acid linker, has been suggested by Holm and Larsen in WO 98/11126. Thus, $Y^C$ may specifically be a radical $Y^{\prime c}$ with the formula —O—CH(R)—C(=O)-(peptide having 1–7 amino acids) where R is a radical as defined in WO 98/11126. The preferred embodiments described in WO 98/11126 also applies in this case.

In one interesting embodiment of the invention the total molecular weight of a peptide of the general formula IV is below about 3,000 g/mol, irrespective of the actual N- and/or C-terminal groups employed.

In another interesting embodiment, the peptide of the invention comprises more than one peptide fragment as defined in formula I above and as will be understood from the examples provided herein, a very promising approach for incorporation of two or more peptide fragments, as defined above, is to attach each of the peptide fragments to a common scaffold.

In principle, various polyfunctionel molecules, such as di-, tri-, tetra-, and pentafunctionel molecules, which are capable of reacting with the N-terminal and/or the C-terminal of a peptide fragment as defined above can be used as the scaffold to which the peptide fragments are attached. However, in a preferred embodiment of the invention, the common scaffold is an L- or D-diamino acid of the general formula V

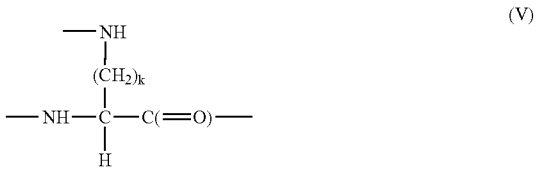

wherein k is an integer in the range from 1 to 6, preferably in the range from 2 to 5, such as 3 or 4.

Preferred examples of amino acids of the general formula V is L-lysine, D-lysine, L-ornithine and D-ornithine, in particular L-lysine.

Thus, it should be understood that the C-terminal amino acid of a first peptide fragment (i.e. the $X^9$ amino acid) is coupled to the α-amino group of the scaffold and that the C-terminal amino acid of a second fragment is coupled to the α-amino group of the scaffold with the general formula V. However, for symmetry reasons it may be advantageous to incorporate one or more linkers between the C-terminal of the peptide fragment and the scaffold to which the peptide fragment is attached.

Thus, in an interesting embodiment of the invention one or more of the peptide fragments are linked to a scaffold of the general formula V as defined above, via one or more ω-amino acids linkers of the general formula VI

$$H_2N-(CH_2)_j-COOH \qquad (VI)$$

wherein j is an integer in the range from 1 to 6, preferably in the range from 1 to 4, such as in the range from 1 to 3, e.g. 1, 2 or 3. Specific examples of suitable ω-amino acids of the general formula VI are e.g. glycine, α-alanine and γ-amino butyric acid, in particular glycine and α-alanine.

This being said, it will be understood by the skilled person that several other possibilities exist for linking two or more peptide fragments of the general formula I to a common scaffold. The peptide fragments may for example be incorporated in, or conjugated with, a molecular carrier such as a protein, e.g. human albumin and other mammalian albumins; diphteria toxin, ricin toxin and human enzymes for activation for of prodrugs, e.g. recombinant human betaglucuronidase; interleukins and other cytokines which activates cell-mediated attack on tumour cells; human immunoglobulins, e.g. IgG; human protease inhibitors, such as alpha-2-antiplasmin, alpha-1-antitrypsin, inter-alpha-trypsin inhibitor, bikunin, Kunitz-type protease inhibitors, kallistatin, secretory leukoprotease inhibitor (SLPI), elafin, or tissue inhibitors of metalloproteases such as TIMP-1, TIMP-2, TIMP-3 and TIMP-4. Other interesting examples of scaffolds are polypeptides, e.g. polylysines, polyhistidines or polyornithines as well as natural or synthetic polymeric molecules such as natural and synthetic polysaccharides and derivatives thereof, for example dextrans and dextranderivatives, starches and starch derivatives, cellulose derivatives, amylose and pectin or synthetic polymers having functional groups such as polyvinyl alcohols, polyallyl alcohol, polyethylene glycols and substitiuted polyacrylates.

It is important, of course, that the molecular carrier (i.e. the common scaffold) possesses at least two, but preferably more, functional groups capable of reacting with either the C-terminal group and/or the N-terminal group of the peptide fragment. Very interesting scaffolds of the invention are therefore such scaffolds which have a dendritic structure carrying a plurality of amino, carboxy, hydroxy and/or thiol groups.

Recently fusion proteins or chemical conjugates have been constructed which contain a uPAR ligand sequence together with a partner protein that sterically hinders accessibility of neighbouring cell-surface receptors and prolongs the half-life of the competitor in the blood circulation. The range of suitable fusion or conjugate protein partners is of course limitless, and includes already uPA or plasmin inhibitors, toxins and antibodies. However, as well as enabling interference with the cell-surface proteolytic system of tumour cells, this range of partner proteins for antagonists can be extended to facilitate the specific targeting of uPAR15 expressing cells. For example this could employ enzymes which process prodrugs (using e.g. ADEPT: K. Bagshawe (1995) *Drug. Develop. Res.* 34:220–230) or antibodies directing cell-mediated cytotoxic reactions (H. Wolf et al. (1994) *Rec. Results Cancer Res.* 135:185195) or even packaged delivery systems (e.g. virosomes: R. Bron et al. (1994) *Biochemistry* 33:9110–9117) may exploit many different methods of attack on tumour cells which display uPAR on their surface. Thus, following peptide synthesis, the non-coding amino acid peptide sequence of the general formula I can be chemically conjugated to any of the above mentioned scaffolds. Examples of methodologies for the preparation of fusion proteins (recombinant joining together of two protein sequences) are given in Min et al., Cancer Research 56:2428–2433 (1996) and in Kobayachi et al., J. Biol. Chem. 270:8361–8366 (1995).

Specific examples of polymeric carrier molecules which may act as a "common scaffold" are e.g. human serum albumin, human lysozyme (a naturally occurring low molecular weight basic protein), polylysine comprising from 3 to 10 free lysine residues, etc. An important issue in connection with the selection of polymeric carrier is the antigenicity, which will be a limiting factor, as will be known for the person skilled in the art.

It should be understood that the peptides of the invention may also be in the form of a salt thereof, of which pharmaceutically acceptable salts are especially relevant. Salts include acid addition salts and basic salts. Examples hereof are hydrochloride salts, hydrobromide salts, sodium salts, calcium salts, potassium salts, etc. Pharmaceutically acceptable salts are, e.g., those described in "Remington's Pharmaceutical Sciences", 17. Ed. Alfonso R. Gennaro (Ed.), Mark Publishing Company, Easton, Pa., U.S.A., 1985 and more recent editions, and in Encyclopia of Pharmaceutical Technology. Furthermore, the peptides of the invention may also be present in a hydrate form.

The peptides of the invention may be prepared by methods known per se in the art. Thus, the peptides of the invention may be prepared by standard peptide-preparation techniques such as solution synthesis or Merrifield-type solid phase synthesis using well-known standard protection, coupling and deprotection procedures. Thus, the peptides of the invention may be produced by a solid phase method essentially comprising the following steps:

a) coupling an N-α-protected amino acid to a solid support material, thereby forming an immobilised N-α-protected amino acid, b) removing the N-α-protecting group, thereby forming an immobilised amino acid having an unprotected N-terminal end, c) coupling an additional N-α-protected amino acid in the carboxyl activated form to the N-terminal end of the immobilised amino acid fragment, and repeating the removal/coupling step procedure in step b) and c) until the desired peptide is obtained, and then d) cleaving off the peptide from the solid support material.

The coupling, removal and cleavage step is performed by methods known to the person skilled in the art taking into consideration the protection strategy and the selected solid phase material. In general, however, it is believed that the Boc (tert.butyloxycarbonyl) as well as the Fmoc (9-fluorenylmethyloxycarbonyl) protection strategies are applicable and that peptide bonds may be formed using the various activation procedures known to the person skilled in the art, e.g. by reacting a C-terminal activated derivative (acid halide, acid anhydride, activated ester e.g. HOBt/carbodi-imide-ester, etc.) of the appropriate amino acid with the amino group of the relevant amino acid or peptide as known to a person skilled in peptide chemistry.

Furthermore, it may be necessary or desirable to include side-chain protection groups when using amino acid units carrying functional groups which are reactive under the prevailing conditions. The necessary protection scheme will be known to the person skilled in the art (see e.g. M. Bodanszky and A. Bodanszky, "The Practice of Peptide Synthesis", 2. Ed, Springer-Verlag, 1994, J. Jones, "The Chemical Synthesis of Peptides", Clarendon Press, 1991, and A. Dryland and R. C. Sheppard (1986) J. Chem. Soc., Perkin Trans. 1, 125–137). Examples of suitable solid support materials for use in the solid phase synthesis of the peptides are e.g. functionalised resins such as polystyrene, polyacrylamide, polydimethylacrylamide, polyethyleneglycol, cellulose, polyethylene, polyethyleneglycol grafted on polystyrene, latex, dynabeads, etc.

In addition, it may be necessary or desirable that the C-terminal amino acid of the peptide is attached to the solid support material by means of a common linker such as 2,4-dimethoxy-4'-hydroxy-benzophenone, 4-(4-hydroxymethyl-3-methoxyphenoxy)-butyric acid, 4-hydroxy-methylbenzoic acid, 4-hydroxymethyl-phenoxyacetic acid, 3-(4-hydroxymethylphenoxy)propionic acid, and p-[(R,S)-a[1-(9H-fluoren-9-yl)methoxy-formamido]-2,4-dimethoxybenzyl]-phenoxy-acetic acid.

In cases where N-substituted amino acids (such as N-substituted glycines) are incorporated into the fragment of the peptide of the invention, the peptides of the invention may in part be prepared by methods described for the preparation of peptoids to provide petide-peptoid hybrids known as peptomers (Østergaard, S. and Holm, A. (1997, Peptomers: a versatile approach for the preparation of diverse combinatorial peptidomimetic bead libraries. Mol. Divers. 1997, December, 3(1):17–27; and Zuckermann, R. N., Kerr, J. M., Kent, S. B. H. and Moss, W. H. (1992) Efficient method for the preparation of peptoids [oligo(N-substituted glycines)] by submonomer solid-phase synthesis. J. Am. Chem. Soc. 114, 10646–10647). N-substituted glycines can be inserted at any point of the growing peptide (or peptomer) chain. The new linkage may be termed a peptoid and comparison of their backbones reveals that the side chain functionality of a peptoid moiety is attached to the amide nitrogen as opposed to the α-carbon in the standard peptide backbone.

One way to assemble the peptoid moiety to a pre-existing chain is from the two submonomers, bromoacetic acid and an amine. The coupling of bromoacetic acid to the amino terminal of a pre-existing peptide or peptomer, or to an amino group on the polymersupport resin, using a carbodiimide, is followed by addition of a primary amine. This sequence of reactions can be repeated as desired. Another way to assemble the peptoid is from the C-terminal end of the peptide or peptomer by reversing the coupling order. To the C-terminal portion of a pre-existing peptide or peptomer is coupled a primary amine, using a carbodiimide, to give a peptoid linkage to which is added bromoacetic acid. This sequence of reactions regenerates a carboxylic acid amenable to further peptide or peptoid assembly.

Among the real advantages of peptoids (i.e. peptides comprising N-substituted amino acids, such as N-substituted glycines) relative to other unnatural peptide-like polymers is their ease of synthesis, the availability of a wide range of monomers (essentially, all primary amines are suitable units for peptoid synthesis), and their high stability towards proteases. Moreover, peptoids allow for a refinement in the shape of the peptide by effectively allowing a side chain to be transposed from the α-carbon of an amino acid to its amine. Given the number of amino acids and primary amines amenable to this methodology and their putative combinations within a peptomer chain, the extent of the peptomer library is immeasurable giving diverse peptidomimetic bead libraries.

The peptides of the invention may be cleaved from the solid support material by means of an acid such as trifluoracetic acid, trifluoromethanesulfonic acid, hydrogenbromide, hydrogenchloride, hydrogenfluoride, etc. optionally in combination with one or more "scavengers" suitable for the purpose, e.g. ethanedithiol, triisopropylsilan, phenol, thioanisole, etc., or the peptides of the invention may be cleaved from the solid support by means of a base such as ammonia, hydrazine, an alkoxide, such as sodium ethoxide, an hydroxide, such as sodium hydroxide, etc.

Another possible strategy is to separately prepare two or more of the sequences constituting the peptide of the invention by solution synthesis, solid phase synthesis, recombinant techniques, or enzymatic synthesis, followed by coupling of the two (or more) sequences by well-known segment condensation procedures, either in solution or using solid phase techniques or a combination thereof.

In the research carried out in connection with the present invention a large number of peptides have been screened for the desired activity (i.e. inhibition of the uPA/uPAR interaction). As will be understood from the examples provided herein the initially screened peptides were synthesised using the so-called "bead library technology" approach by Lam et al. Nature 354:82–84 (1991) and the principle of the method is described in FIG. 1.

The method is initiated by the distribution of all the resin beads in portions of equal size. An amino acid (monomer) is attached (coupled) to each portion but only one type of monomer to each portion. After coupling has completed the portions are combined and mixed thoroughly before the next dividing step. FIG. 1 illustrates the synthesis by using only 3 building blocks and two steps, but the number of building blocks and synthesis steps is of course optional.

The procedure generates a very large library of compounds (peptides) in a random fashion. The important thing is that each bead only represents one sequence, i.e. an amount of e.g. 2 million beads will generate 2 million different peptides.

The screening procedure is accomplished by methods known in the art, i.e. the library is typically incubated with a water soluble receptor of interest (target receptor). Usually alkaline phosphatase is coupled either directly or indirectly to this receptor. This enzyme can be attached to the target receptor by the binding of a phosphatase conjugated antibody directed against the target receptor, or alkaline phosphatase may be conjugated to streptavidin which is then directed against a biotinylated form of the target receptor or a biotinylated anti-receptor antibody. By using conventional immunochemical techniques, in which the enzyme catalyses a reaction which generates a colour, active beads that bind to the target receptor can be made visible to the eye. Once the active beads are found they are isolated and the sequence is analysed one bead at a time using a protein sequencer. Following this, the peptide or peptides of interest may be synthesised in full-scale as described above.

Although the peptides of the invention in general exhibit a high affinity for uPAR, low off-rates and high potency in a cell-binding system there may, however, be a variation between the potency of the individual peptides described herein. Therefore, the present inventors have provided suitable assays enabling the person skilled in the art to select effective and preferred peptides based on such assays.

Examples of these assays are given in the experimental section of the present description.

In the present context, the term "a receptor binding form of uPA" is intended to mean any form of uPA possessing a site that binds to a site at a uPAR, that is to say that the uPA contains the uPAR binding site. The receptor binding form of uPA can thus be pro-uPA, uPA, an amino-terminal fragment of uPA (ATF-uPA), a uPA that is irreversibly inhibited by e.g. diisopropyl fluorophosphate (DFP), p-nitrophenyl-p'-guanidinobenzoate (NPGB), or any other modification of uPA that can bind to a uPAR.

The usage of the term "a uPAR" indicates that even though the polypeptide part of uPAR in a species might be the same for all uPARs, there is a plurality of uPARs as for example the carbohydrate part or the mechanism of surface attachment of the uPAR can be different. It may even be that some cells, e.g. cancer cells, have substantially different uPARs which might have important therapeutic significance as it might be possible to block the binding of uPA to uPARs residing on a cancer cell without affecting the binding of uPA to uPARs on non-pathological cells or of specifically killing cancer cells that express uPAR.

The enzyme urokinase-type plasminogen activator (uPA) has only one well-defined macromolecular substrate, namely plasminogen. By cleavage at $Arg^{560}$, plasminogen is activated to the broad spectrum protease plasmin. By the term "inhibiting the activation of plasminogen to plasmin by inhibiting the binding of a receptor-binding form of uPA to a uPAR" is therefore meant that this activation by uPA is substantially inhibited or a situation where the activation is sufficiently inhibited so as to inhibit or reduce the undesired effect of the plasmin, i.e. the proteolytic activity of plasmin is prevented or counteracted.

The prevention of the binding of a receptor binding form of uPA to a uPAR is, e.g. suitably performed by blocking the uPAR by administration, to the mammal, of a substance binding to the uPAR so as to occupy a site of the receptor to which a receptor binding form of uPA is normally bound, the substance being administered in an amount effective to reduce the binding of the receptor binding form of uPA to the receptor. In the present context the term "blocking the uPAR" means that a substance that is not able to activate plasminogen to plasmin is bound to uPAR, preferably by a substantially irreversible binding, thereby preventing a receptor binding form of uPA from catalyzing the conversion of cell surface bound plasminogen into plasmin.

The requirements of the peptides of the invention to function as efficient inhibitors of the uPA/uPAR system is that on the one hand the peptide should have a high affinity for the receptor, and on the other hand that the peptide should "stay" on the receptor as long as possible. Thus the peptide/uPAR system should preferably exhibit slow dissociation kinetics (the so-called "off-rate"), which may conveniently be expressed as the dissociation rate constant $k_{diss}$.

Therefore, assays have been developed which give an assessment of the capability of the peptide/uPAR system to exert the desired affinity and/or kinetic properties, i.e. to assess the capability of the peptides of the invention to function as inhibitors of the uPA/uPAR system and thereby impede efficient binding of uPA to the receptor.

Based thereon, peptides of the invention which are especially preferred are peptides which, when tested in the Blacore Binding Assay described herein, have a dissociation rate constant ($k_{diss}$) relative to the Growth Factor Domain of uPA (GFD) of at the most 5.0, such as at the most 4.0, e.g. at the most 3.0, preferably at the most 2.0, such as at the most 1.5, e.g. at the most 1.0, most preferably at the most 0.75, such as at the most 0.5, e.g. at the most 0.25, at the most 0.1, at the most 0.05, or at the most 0.01.

On the other hand, the uPA/uPAR Binding Assay disclosed in the examples, is a test for determining the thermodynamic binding properties of a given peptide to the receptor in a cell-binding system. Thus, very interesting peptides of the invention are such peptides which when tested in the uPA/uPAR Binding Assay described herein, are able to inhibit the binding of radio-labelled Amino Terminal Fragment (ATF) of uPA to cell-surface uPAR by 50% at a concentration of at the most 50 nM, such as of at the most 35 nM, e.g. of at the most 25 nM, preferably of at the most 10 nM, such as of at the most 7.5 nM, e.g. of at the most 5 nM, most preferably of at the most 3 nM, such as of at the most 2 nM, e.g. of at the most 1 nM, in particular of at the most 0.5 nM, such as of at the most 0.1 nM, e.g. of at the most 0.01 nM.

Evidently, it is preferred that a peptide of the invention fulfils one or preferably both of the above criteria on at least the stated lowest level, more preferably on the intermediate level and most preferably at the stated highest level.

Based on experiments of the above-mentioned type carried out so far, examples of especially interesting peptides are such peptides, wherein the at least one peptide fragment is selected from the group consisting of dChaFsrYLWS, SL ChaFsQYLWS, eChaFsyYLWS, DChaFsrYLWS, D ChaFSrYLWS, dChaFSrYLWS, tChaFsrYLWS, d ChaFsrYL$^2$nAS, DChaFsRYLWS, DChaFsrYL$^1$nAS, e ChaFsYYLWS, D-Cha-F-s-r-L-L-W-h, D-Cha-F-s-r-Cha-L-W-I, D-Cha-F-s-r-Y-L-Nal-h, D-Cha-F-s-r-DMB-f-TRA-MEA, D-ChaF-s-r-DMB-f-Bzl-MEA, D-Cha-F-s-r-DMB-f-AMN-MEA and D-Cha-F-s-r-DMB-f-DMB-I wherein Cha designates α-cyclohexyl-L-alanine, $^1$nA designates β-1-naphthyl-L-alanine, $^2$nA designates β-2-naphthyl-L-alanine, capital letters designate L-amino acids, lower case letters designate D-amino acids, βA designates β-alanine, DMB designates N-(2,3-dimethoxybenzyl)glycine, TRA designates N-(3-indolylethyl)glycine, MEA designates N-(2-methoxyethyl)glycine, Bzl designates N-benzylglycine and AMN designates N-(methylnaphthalyl) glycine.

Other examples of specific peptides which fulfil the requirements set forth above are peptides selected from the group consisting of α-[DChaFsrYLWSG]-ϵ-[D ChaFsrYLWSG](L)-lysine, α-[D ChaFsrYLWSGβA]-ϵ-[DChaFsrYLWSG]-(L)-lysine, and α-[DChaFsrYLWSβA]-ϵ-[DChaFsrYLWS]-lysine.

where βA designates β-alanine, and Cha, capital letters and lower case letters are as defined above.

The present invention also relates to a test system comprising methods for selecting a peptide antagonist which is suitable for preventing or counteracting localized extracellular proteolytic activity of plasmin in a human. The inhibition of the proteolytic activity of plasmin is performed by inhibiting the activation of plasminogen to plasmin by inhibiting the binding of a receptor-binding form of uPA to a uPAR in the human.

The method comprises providing a modified uPAR of a non-human mammalian species, said modified uPAR being modified in a manner which renders it capable of being antagonized by a peptide antagonist while retaining its capability of binding to a receptor-binding form of uPA of said mammal species substantially unchanged, in a model system for assessing antagonism of uPA/uPAR binding and comprising said modified uPAR carried by cells of the non-human mammal species as well as a receptor-binding form of uPA of the species. The method will be performed by subjecting a panel of peptides to assessment in the model system and selecting, as peptide antagonists, such peptides among the panel of peptides which, in the model system, result in a degree of antagonism of the binding of the uPA to the modified uPAR which is similar to the degree of antagonism obtained by using an ATF-fragment of said uPA. The degree of antagonism is preferably at least one-tenth of the degree of antagonism obtained by using an ATF-fragment, more preferably at least one-fifth of the degree of antagonism obtained by using an ATF-fragment, more preferably at least one-quarter of the degree of antagonism obtained by using an ATF-fragment, even more preferably half of the degree of antagonism obtained by using an ATF-fragment, preferably three-quarters of the degree of antagonism obtained by using an ATF-fragment, most preferably equal to or higher than the degree of antagonism obtained by using an ATF-fragment.

The non-human species of the screening method may be selected from the group consisting of mouse, hamster, rat, dog, cat, cow, rabbit or non-human primates or any other mammal.

Furthermore, the model system can comprise human, non-human or non-human primate tumour cells in an environment of the non-human cells. The modified uPAR may be a uPAR the natural counterpart of which is associated with the particular tumour cells or the environment of the non-human cells or both. Also the receptor-binding form of uPA may be supplied by either the particular tumour cells or the environment of the non-human cells.

The described model system can be comprised of one or more of the following test systems:

1) a screening assay in which the possible inhibition of uPA/uPAR interaction by antagonist is determined by adding the antagonist to the system comprising the modified uPAR and solubilized uPA, uPA bound to uPAR being detected by being labelled or by means of a labelled anti-uPA antibody, or adding the substance to a system comprising immobilized uPA and solubilized uPAR, uPAR bound to uPA being detected by being labelled or by means of a labelled anti-uPAR antibody,
2) an assay in which the possible inhibition of uPA/uPAR interaction by the antagonist is determined by adding the antagonist to a system comprising uPAR and radiolabelled uPA or a derivative thereof, cross-linking any uPAR bound to uPA and detecting any cross-linked product by SDS PAGE and autoradiography,
3) an assay in which the possible inhibition of binding of uPA to uPAR on the surface of cultured cells is determined by adding the antagonist to a system comprising radiolabelled uPA or a derivative thereof and cells carrying uPAR and detecting any uPA or derivative binding to uPAR by gamma counting of the cells,
4) an assay in which the possible inhibition of cell surface plasminogen activation by receptor-bound exogenous pro-uPA is determined by adding the antagonist to cells carrying uPAR and subsequently adding pro-uPA, followed by measurement of plasmin generation on the cell surface,
5) an assay in which the possible inhibition of cell surface plasminogen activation by receptor-bound endogenous pro-uPA is determined by incubating cells carrying uPAR and producing pro-uPA with the antagonist, followed by measurement of plasmin generation on the cell surface,
6) an assay in which human or non-human tumour cells are inoculated into an immunocompromised mouse and recovered from the mouse after treatment with the antagonist, followed by measurement of the reduction of bound uPA on the tumour cell surface using flow cytometric methods,
7) administering a substance which has been established to inhibit uPA/uPAR interaction to a immunodeficient mouse which also lacks a functional gene for uPAR, said mouse being susceptible to invasion or metastasis by human or non-human tumour cells and said mouse being inoculated with human or non-human tumour cells which are known to invade and/or metastasize in the presence of uPA and uPAR and which are capable of invasion and/or metastasis in the mouse, and measuring the inhibition of the invasion and/or metastasis of the human or nonhuman tumour cells in the mouse.)

In 6) of the above test systems the amount of uPA bound to uPAR on the surface of the tumour cells is then determined by either 1) acid elution and immunocapture assay (see e.g. Tapiovaara et al, 1993, Blood 82, 914–919) or 2) flow cytometry with anti-uPA antibody fluorescent staining.

In 7) of the above test systems the tumour cells inoculated into the mouse may, prior to their inoculation, have been transduced with the lacZ gene which encodes the enzyme β-D-galactosidase. This enzyme will give rise to a blue staining when subjected to the substrate X-gal. Thus, this system makes it possible to obtain a distinct colour difference between the human cancer cells, and the mouse's own cells, thereby very considerably facilitating detection and quantitation of invading cells and metastases.

The modified uPAR of the screening method is a non-human uPAR in which the amino acid sequence has been modified by substituting one or more amino acids of the non-human uPAR. The modification is obtained by substituting 10 amino acids, preferably 5 amino acids, more preferably 3 amino acids, even more preferably 2 amino acids, most preferably 1 amino acid. The region wherein the substitution of the amino acid(s) is/are preferred is located in uPAR domain III loop 3 (see FIG. 9). The preferred amino acid residue(s) to be substituted is/are the amino acid(s) of the non-human uPAR corresponding to the amino acid residues $His^{249}$, $Ser^{254}$ and $Asn^{256}$ of the human uPAR sequence, most preferably the amino acid of the non-human uPAR to be substituted is the amino acid corresponding to amino acid $His^{249}$ of the human uPAR sequence (marked with an arrow in FIG. 9). The substitution in the amino acid sequence of the non-human uPAR is preferably so that the amino acid at the substituted position in the non-human uPAR is the same as the amino acid of the human uPAR, i.e. the amino acid marked with an arrow in FIG. 9 of the nonhuman uPAR sequences is a His residue, e.g. $Gly^{272}$ in the mouse uPAR sequence (NCBI number sp/P35456) is substituted with $His^{272}$, $Gly^{273}$ in the rat uPAR sequence (NCBI numbers gi/2253496, pir//S42152, and sp/P49616) is substituted with $His^{273}$, $Ser^{268}$ in the bovine uPAR sequence (NCBI number sp/Q05588) is substituted with $His^{268}$. In the hamster the $Gly^{251}$ (according to the sequence alignment in the published hamster uPAR sequence (Fowler et al, Thromb. Haem. 1998, 80, 148–154)) is substituted with $His^{251}$. The non-human sequences corresponding to the critical histidine in the human uPAR sequence are also obvious from the alignment diagram published in Fowler et al., Thromb. Haem. 1998, 80, 148–154.

The method by which this amino acid substitution is obtained could be any method known in the art for substituting amino acid sequences in proteins, e.g. gene knock-in/gene knock-out technology (Hanks et al 1995, Science 269, 679–682). In the case of using a mouse as the non-human mammal of the screening method, the mouse may be a transgenic mouse containing the modified uPAR.

The present invention also relates to a pharmaceutical composition comprising a peptide as defined above. Such pharmaceutical compositions may be in a form (e.g. in liquid, powdered or lyophilised form) adapted to oral, parenteral (intravenous, intraperitoneal, intramuscular, subcutaneous) rectal, intranasal, dermal, vaginal, buccal, ocularly or pulmonary administration, and such compositions may be prepared in a manner well-known to the person skilled in the art, e.g. as generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker.

Thus, the peptides used in this invention may be prepared as formulations in pharmaceutically acceptable media, for example, saline, phosphate buffered saline (PBS), Ringer's solution, dextrose/saline, Hank's solution, and glucose. The compositions may contain pharmaceutically acceptable auxiliary substances as required to approximate physiological conditions, such as buffering agents, tonicity adjusting agents, wetting agents, emulsifying agents, detergents, and the like. Additives may also include additional active ingredients, e.g. bactericidal agents, stabilizers, or preservatives. The amount administered to the patient will vary depending upon what is being administered, the purpose of the administration, such as prophylaxis or therapy, the state of the host, the manner of administration, and the like.

The pharmaceutical compositions are typically intended for transdermal or parenteral administration, e.g. intravenously, subcutaneously, or intramuscularly. Orally administrative forms are also desired and can be provided by modifying the composition to bypass the stomach environment. The composition can be used for prophylactic and/or therapeutic treatment. Preferably, the pharmaceutical compositions are administered intravenously. Thus, the compositions may comprise a peptide antagonist according to the invention which is dissolved or suspended in an acceptable carrier, preferably an aqueous carrier. Such compositions may be sterilised by conventional sterilisation techniques, or may be sterile filtered.

The resulting aqueous solutions may be packaged for use as is, or lyophilised, the lyophilised preparation being combined with a sterile aqueous carrier prior to administration. The peptide antagonist may also be administered with a second biologically active agent, such as a standard chemotherapeutic agent. Such agents include but are not limited to vincristine, daunorubicin, L-asparaginase, mitoxantrone and amsacrine.

In therapeutic applications, the pharmaceutical compositions are administered to a patient in an amount sufficient to produce the desired effect, defined as a "therapeutically effective dose". The therapeutically effective dose of a peptide antagonist according to the invention will vary according to, for example, the particular use for which the treatment is made, the manner of administration, the health and condition of the patient, and the judgement of the prescribing physician. A therapeutically effective dose can be estimated by means of the desirable plasma concentration, which is large compared to the known affinity (binding constant) of the peptide for the receptor. A level of at least about 0.3 nM would often be desirable. A plasma level of at least about 10 nM would often be required, preferably at least about 100 nM, and if possible with due regard to the toxicity, side effects, etc., at least about 1 µM. This level should be maintained for a period of e.g. one month in order to suppress tumour growth.

For example, the dose for continuous infusion will typically be in the range of about 0.1 mg to about 1000 mg per day for a 70 kg patient, preferably between about 1 mg and about 100 mg. The dose will typically be between 100 ng/kg/day and 10 µg/kg/day.

The concentration of the peptide antagonist in the pharmaceutical formulations can vary widely, i.e. from about 0.1% to about 10%, preferably between about 0.5% and about 5% (wt/vol). The concentration will usually be selected primarily by fluid volumes, viscosities, etc., in accordance with the particular mode of administration selected. Thus, a typical pharmaceutical composition for intravenous infusion could be made up to contain 500 ml of dextrose/saline solution and 50 mg of the peptide antagonist.

For solid compositions, conventional non-toxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable non-toxic composition is formed by incorporating normally employed excipients, such as those carriers previously listed, and generally 10–95% of active ingredient, that is, a peptide antagonist substance, preferably 25–75%.

For aerosol administration, the peptide antagonist is preferably supplied in finely divided form along with a surfactant and propellant. Typical percentages of peptide antagonists are 0.01–20% by weight, preferably 1–10%. The surfactant must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arbitol, mannitol, sorbitol, the hexitol anhydrides derived from sorbitol, and the polyoxyethylene and polyoxypropylene derivatives of these esters. Mixed esters, such as mixed or natural glycerides may be employed.

The surfactant may constitute 0.1–20% by weight of the composition, preferably 0.25–5%. The balance of the composition is ordinarily propellant. Liquified propellants are typically gases at ambient conditions, and are condensed under pressure. Among suitable liquified propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided polypeptide(s) and surfactant. The ingredients are thus maintained at an elevated pressure until released by action of the valve.

To enhance the serum half-life, the peptide antagonist may be encapsulated, introduced into the lumen of liposomes, prepared as a colloid, or other conventional techniques may be employed which provide an extended lifetime of the peptides. Thus, in certain embodiments, the peptide antagonist may be encapsulated in a liposome. A variety of methods are available for preparing liposomes, as described in, e.g. U.S. Pat. No. 4,235,871; U.S. Pat. No. 4,501,728; U.S. Pat. No. 4,837,028 and W. H. Gotlieb et al (1992) *Cytokine* 4:385–930.

As shown in Example 9 herein, the inclusion of D-amino acids in the peptides of the invention (as well as "dimer"

formation) render such peptides significant less susceptible to proteolytic degradation. For example, the most promising peptides thus far are the "dimers" AE118 and AE120 (The structures of AE118 and AE120 are [DChaFsrYLWSG]$_2$-K and α-[DChaFsrYLWSGβA]-ε-[DChaFsrYLWSG]-L-lysine, respectively) only showing a slight reduction in its ability to inhibit ATF binding to monolayer cultures of human MDA-MB-231 breast cancer cells after incubation in 10% mouse serum for up to 24 hours at 37° C.

The "monomer" AE78 (i.e. the so-called "Clone 20" having the sequence: AEPMPHSLNFSQYLWYT (SEQ ID NO: 2)), on the other, lost the majority of its inhibitory activity after incubation with 10% mouse serum for 24 hours even though the concentration was 1000 fold (3 orders of magnitude) higher than that of AE118.

These findings open up new prospects of administering the peptide of the invention and, as mentioned above, it may even be realistic to administer a peptide of the invention orally if the peptide comprises at least one D-amino acid, e.g. at least two D-amino acids, as it is envisaged that such D-amino acid-containing peptides may survive the proteolytic barriers prevailing in e.g. the gastrointestinal environment. Further proteolytic stability is conferred when, as mentioned above, the fragment comprises one or more N-substituted amino acids, such as one or more N-substituted glycines. The prospect of oral administration seems most realisable in instances where the fragment comprises both D-amino acids and N-substituted amino acids, such as N-substituted glycines.

Accordingly, peptides of the invention with are considered as being of particular interest, are such peptides which, when incubated for 24 hours at 37° C. in 10% mouse serum and subsequently tested in the uPA/uPAR Binding Assay, as defined herein, has an IC$_{50}$ value relative to the corresponding non-incubated peptide (i.e. IC$_{50, \text{ non-incubated}}$/ C$_{50, \text{ incubated}}$) of at least 0.5, such as at least 0.6, e.g. at least 0.7, preferably at least 0.8, such as at least 0.9, e.g. at least 0.95, in particular at least 0.99.

Furthermore, the present invention relates to a peptide as defined above for use as a medicament, and to the use of a peptide as defined above for the manufacture of a medicament for the treatment of cancer. It is contemplated that the peptides of the present invention are effective drugs in the treatment of a variety of different cancers. However, as the most malignant and fast lethal cancers are known to overexpress uPAR it is presently believed that the most promising aspects of the present invention relates to the treatment of these malignant and fast lethal cancers, such as acute myeloid leukaemia, malignant gliomas of the brain, and gastric cancer.

BRIEF DESCRIPTION OF THE DRAWINGS

FIG. 9: Sequence comparison of the relevant amino acids subjected to alanine mutagenesis in human (SEQ ID NO:3) uPAR to the corresponding residues of hamster (SEQ ID NO:4), mouse (SEQ ID NO:5), rat (SEQ ID NO:6), and bovine (SEQ ID NO:7) uPAR.

EXAMPLES

General

Peptide Synthesis

Figure 1:
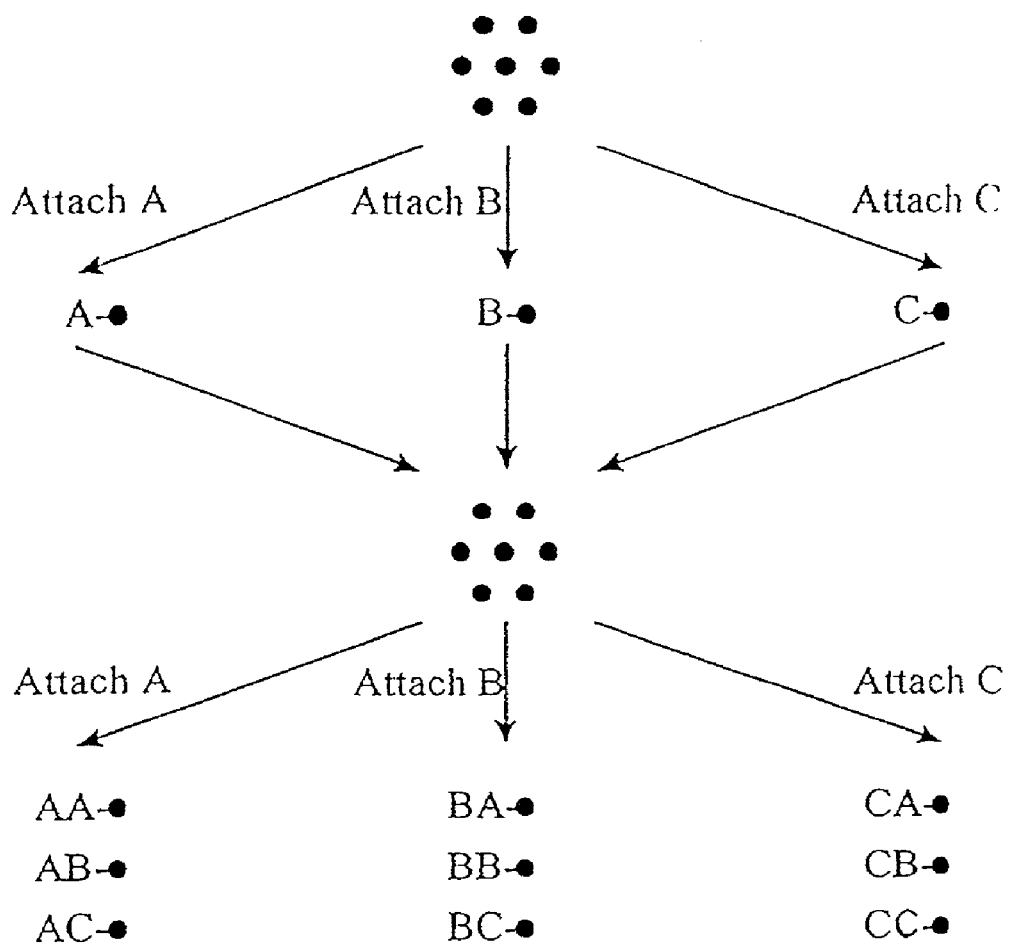
FIG. 1: The principle of the library technology.
The figure shows the "divide, couple and recombine" procedure. A, B and C are the building blocks used in the synthesis step. The essential feature of the technique is the unique sequence on each bead.

The chain elongation steps of the solid-phase peptide synthesis were carried out manually using polyethylene syringes as reaction vessels. Synthesis was performed on KA-resin with preloaded Fmoc-amino acids on the acid-labile linker. Five equivalents of Fmoc-amino acids activated by 1-hydroxy-7-benzotriazole (HOBt) and N,N'-diisopropylcarbodiimide were used in the coupling steps and were allowed to react for more than 2 h. The Fmoc protecting group was removed with 20% piperidine in dimethylformamide for 15–20 min. For cleavage, peptide-resins were treated for 1.5 h with 85% TFA containing 5% of phenol, mercaptoethanol, and thioanisole, respectively. The filtrates were concentrated by nitrogen flushing, and peptides were subsequently precipitated from, and washed four times with, diethyl ether. Peptides were finally dissolved/suspended in glacial acetic acid, lyophilised, redissolved in 10% acetic acid, and lyophilised again. Analytical HPLC analysis was performed on a C$_{18}$ column using Waters 600E equipped with Waters photodiode array detector. A 25 min linear gradient from buffer A (0.1% TFA, 9.9% H$_2$O, 90% CH$_3$CN)

was used. If considered necessary peptides were purified on a preparative scale. The correct identities of the peptides were confirmed by matrix assisted laser desorption ionisation mass spectroscopy or electrospray ionization mass spectrometry. The purity was checked by reverse phase HPLC.

The following peptides were synthesised using standard methodologies:

| | |
|---|---|
| dChaFsrYLWs | (Code: dCha) |
| eChaFsyYLWS | (Code: AE100) |
| tChaFsrYLWS | (Code: AE108) |
| DchaFsrYLWS | (Code: AE105) |
| DChaFsrGYLWS | (Code: AE116) |
| DChaFsrβAYLWS | (Code: AE117) |
| DChaFSrYLWS | (Code: AE106) |
| dChaFSrYLWS | (Code: AE107) |
| SLChaFsQYLWS | (Code: Lcha) |
| dChaFsrYL²nAS | (Code: AE109) |
| DChaFsRYLWS | (Code: AE110) |
| DchaFsrYL¹nAS | (Code:.AE114) |
| eChaFsYYLWS | (Code: AE115) |
| SLNFSQYLWS | (Code: AE68) (SEQ ID NO: 1) |
| AEPMPHSLNFSQYLWYT | (Code: AE78) (SEQ ID NO: 2) |
| arFhhYLWS | (Code: AE104) |
| LNFsQYLWS | (Code: AE111) |
| DFFsrYLWS | (Code: AE112) |
| DNFsrYLWS | (Code: AE113) |

The "multimeric" peptides were synthesised by standardised peptide synthesis methodologies using a orthogonal protection strategy (e.g. as described by Cwirla et al. Science, Vol 276, 1997, pp 1696–1699):

| | |
|---|---|
| [DChaFsrYLWSG]$_2$-K | (Code: AE118) |
| α-[DChaFsrYLWSGβA]-ε-[DChaFsrYLWSG]-K | (Code: AE120) |

(Alternatively, heterogeneous methods well known to peptide chemists for construction of e.g. multimeric antigens for immunisation (D. N. Posnett et al (1988) *J. Biol. Chem.* 263:1719–1725) are also applicable within the present invention.)

Purification of Proteins

The Growth factor-like domain (GFD) of human uPA was produced by endoproteinase GluC digestion of recombinant pro-uPA as described in M. Ploug et al. (1995) *Biochemistry* 34:12524–12534.

A soluble recombinant variant of human uPAR (suPAR) was expressed in Chinese hamster ovary (dhfr) cells. The suPAR protein was purified by immunoaffinity chromatography using an anti-uPAR monoclonal antibody as described in M. Ploug et al. (1993) *Biol. Chem.* 268:17539–17546.

Recombinant human pro-uPA expressed in *E. coli* was provided by Dr. D. Saunders (Grünenthal, Germany). This product can be prepared as described in EP 0496327 A. Two chain active uPA was purchased from Serono (Aubonne, Switzerland).

The amino-terminal-fragment (ATF) of human uPA was provided by Drs. A. Mazar and J. Henkin (Abbott Laboratories, IL). This product can be prepared as decribed by Mazar et al. Fibrinolysis, 6, Suppl. 1, 49–55, 1992.

Binding Studies of Peptides using Biacore Technology

Real:Time Biomolecular Interaction Analysis (BIA)

Association rate constants ($k_{ass}$), dissociation rate constants ($k_{diss}$) and equilibrium binding constants ($k_d$) for various synthetic peptides and receptor binding derivatives of human uPA were determined by surface plasmon resonance (R. Karlsson et al. (1991) *J. Immunol. Meths.* 145: 229–240) using a BIAcore2000™ instrument (Pharmacia Biosensor, Uppsala, Sweden). Due to the low isoelectric point of uPAR (pI≈4.5) terminal sialic acid residues were removed from its N-linked carbohydrates to facilitate chemical immobilisation on the sensor chip. This was accomplished by incubating purified suPAR (1 mg/ml in 50 mM phosphate, 150 mM NaCl, pH 7.4) with 5 μg/ml neuramimidase for 4 hours at 37° C. Such desialylation did not alter the uPA binding kinetics of suPAR (M. Ploug et al. *J. Biol. Chem.*, Vol. 273, 22, 13933–13943, 1998). Coupling of the neuramimidase-treated suPAR to a BIAcore sensor chip was achieved by injection of 20 μg/ml suPAR in 10 mM sodium acetate pH 5.0 for 6 minutes at a flow rate of 5 pI per minute using a carboxymethylated dextran matrix (CM5 sensor chip) preactivated with N-hydroxysuccinimide/N-ethyl-N'-[3-(diethyl-amino)propyl]carbodiimide according to the manufacturer's recommendations. Approximately 1,500–2,000 resonance units (RU) were immobilised by this procedure (corresponding to 1–2 ng suPAR/mm$^2$).

Sensorgrams (RU versus time) were recorded (FIG. 2) at a flow rate of 10 μl per min at 5° C. using several different concentrations of the ligand (synthetic peptides, uPA, the amino-terminal fragment (ATF) of uPA, or the growth factor domain (GFD) of uPA) in the range of 10 to 1000 nM in running buffer (10 mM HEPES, 150 mM NaCl, 3 mM EDTA (pH 7.4) including 0.005% surfactant P-20). Stock solutions of peptides from combinatorial chemistry were made in DMSO (10 mg peptide/ml DMSO). The sensor chip was regenerated at the end of each run by injection of 0.1 M acetic acid, 0.5 M NaCl. Data obtained from parallel mock coupled flow cells (subjected to the coupling procedure in the presence of buffer only) served as blank sensorgrams for subtraction of changes in bulk refractive index. The sensorgrams obtained were analysed by non-linear least squares fitting using BIAevaluation 2.0 software (Pharmacia Biosensor, Uppsala, Sweden) assuming single-site association and dissociation models.

Figure 2:
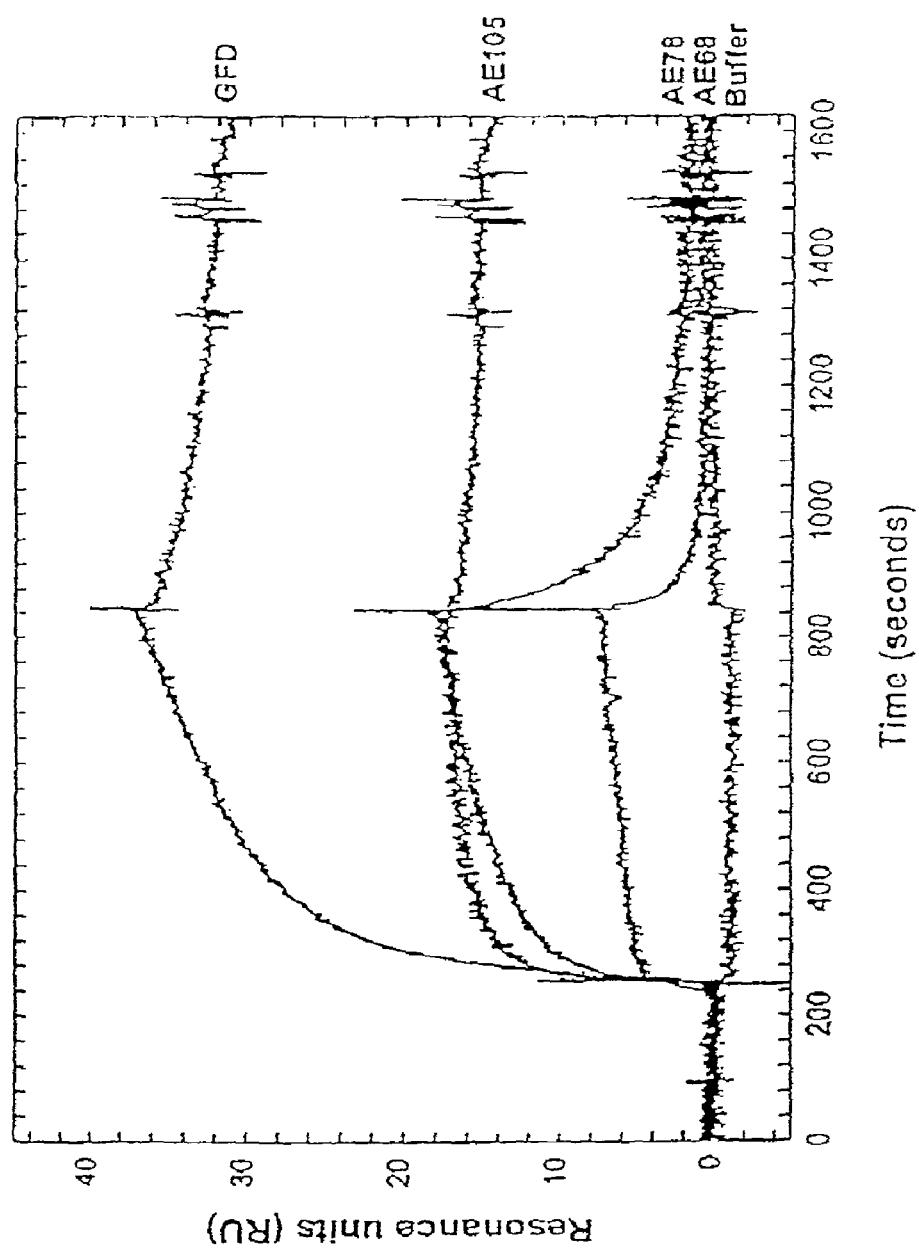
FIG. 2: Binding of peptides by combinatorial chemistry to immobilized suPAR.
The figure shows real-time binding curves (sensorgrams) for the interaction between various ligands and immobilised uPAR measured by surface plasmon resonance (Example 3). The figure shows sensorgrams recorded for 100 nM GFD, 1 μM of AE68, 1 μM of AE78 and 1 μM of AE105 to immobilised, neuramimidase-treated suPAR. Also shown is the sensorgram recorded for a buffer control.

Biacore affinity measurements were made for the peptides described herein as well as for the reference peptides. The results are summarised in Table 2, and typical sensorgrams are shown in FIG. 2.

Example 1

Identification of Critical Residues for Activity

The starting peptide sequence used was the peptide disclosed earlier by Chiron as Clone 20 (R. J. Goodson et al. (1994) Proc. Nat. Acad. Sci. U.S.A. 91:7129–7133). The peptide consists entirely of naturally occurring amino acids:

A E P M P H S L N F S Q Y L W Y T (AE78) (SEQ ID NO:2)

a) The effect of truncation of this peptide was first studied. Truncation was performed by (step-wise) elimination of sets of two amino acids from the C-terminal end and from the N-terminal end. By this procedure a 10-mer peptide was identified as the minimum sequence retaining good activity:

S L N F S Q Y L W S (AE68) (SEQ ID NO:1)

b) An alanine scan of this 10-mer was then performed in order to identify the functionally most important residues. The result obtained was:

S L N F S Q Y L W S (SEQ ID NO:1)

where the underlined residues are considered critical for the activity of the peptide. This finding furthermore suggested that 2 distinct sites exist in the preferred antagonist, which bind to 2 distinct sites in human uPAR.

With respect to the alanine scan performed, the exact experimental conditions are given in M. Ploug et al. (1998) *Biochemistry*, 37:3612–3622.

Example 2

Photochemical Identification of Interaction Sites

The photoaffinity labeling of human uPAR was carried out as described in Ploug et al. (1998) *Biochemistry* 37:3612–3622.

Photoaffinity labeling confirmed that a two-site interaction occurs with the human uPAR molecule, and specifically that:

a) F interacts primarily with Arg53, and to a less extent with Leu66 loop 3 of uPAR Domain I.

b) W interacts with His251 in loop 3 of uPAR Domain III.

Thus, two more or less independently acting binding sites were identified, situated on separate structural domains. This composite binding site is thus possibly assembled through interdomain interactions.

Example 3

Higher Affinity Peptides from Combinatorial Chemistry

In the combinatorial chemistry studies, the following residues underlined) were fixed as shown:

(X)$_{0-3}$E X X Y L W S and a sub-library was synthesised which incorporated unnatural amino acids in the remaining positions. The unnatural amino acids were selected from: 18 D-amino acids: D-Ala, D-Ser, D-Thr, D-Tyr, D-Asp, D-Glu, D-Lys, D-His, D-Arg, D-Asn, D-Gln, D-Pro, D-Leu, D-Val, D-Ile, D-Met, D-Phe, D-Trp, O-benzyl-L-tyrosine, O-benzyl-L-hydroxyproline, N$_{im}$-benzyl-L-histidine, β-2-naphthyl-L-alanine (abbreviated $^2$nA), β-cyclohexyl-L-alanine (abbreviated Cha), D-phenylglycine as well as glycine.

The combinatorial peptide libraries were generated as described in e.g. S. E. Cwirla et al. (1997) *Science* 276: 1696–1699. Thus, 1 gram of TentaGel S amine (Rapp Polymere) resin was washed thoroughly with dimethylformamide (DMF) and 5% diisopropylamine (DIEA) and finally with DMF. Standard Fmoc solid phase peptide synthesis was employed in the generation of the peptidylresin YLWS-Resin using 4 eq of Fmoc-amino acid, DIC and HOBt, respectively, during all coupling steps. The resin was then distributed equally into 25 reaction vessels and coupled with the above-mentioned unnatural amino acids.

After coupling overnight the 25 portions were combined and mixed thoroughly and subsequently the Fmoc group was removed and the resin was again distributed into 25 portion and coupled with the above-mentioned unnatural amino acids to obtain the X-X-Y-L-W-S-resin. The peptidylresin X-X-Y-L-W-S-Resin, where X represents any of the 25 amino acids mentioned above, was coupled with Fmoc-Phe-OH using DIC and HOBt giving the peptidylresin F-X-X-Y-L-W-S-resin. This resin was again used in the divide, mix and recombine procedure, with the exception that small amount of resin was removed before each distribution step as shown in Table 1.

TABLE 1

Removal of resin during the (X)$_{0-3}$-F-X-X-YLWS-resin synthesis

| | | |
|---|---|---|
| X = 0 | about 10,000 beads removed | (FXXYLWS-resin) |
| X = 1 | about 100,000 beads removed | (XFXXYLWS-resin) |
| X = 2 | about 500,000 beads removed | (XXFXXYLWS-resin) |
| X = 3 | the remaining ~2.3 mill beads | (XXXFXXYLWS-resin) |

After the final coupling all resin fractions were washed with DMF, deprotected with 20% piperidine (PIP) in DMF and finally washed thoroughly with tetrahydrofuran (THF). A solution of 85% trifluoroacetic acid (TFA), 5% thioanisole, 5% mercaptoethanol and 5% phenol was added to the peptidylresin, (X)$_{0-3}$-F-X-X-Y-L-W-S-resin, for 1.5 hours and subsequently washed with THF and gradually with 10% AcOH in H$_2$O. Finally the peptidylresin was lyophilised.

The screening for activity was performed in the following way:

The library was incubated with streptavidin alkaline phosphatase diluted 1:10,000 (Sigma (1 mg/ml)) for 45 min in 0.05 M tris-HCl buffer pH 7.4, 0.25 M NaCl, 0.1% gelatine, 0.05% Tween 20. After washing with tris washing buffer (0.05 M tris-HCl, pH 7.4, 0.05% Tween 20, 0.25 M NaCl) staining was accomplished with 5-bromo-4-chloro-3-indolylphosphate in tris-HCl 0.05 M, pH 9.2, 0.1 M NaCl, 0.05 M MgCl$_2$ for 60 min. Active blue beads interacting with streptavidin were removed from the library which was subsequently washed with 8 M guanidiniumchloride and recycled for a second screening with murine anti-uPAR monoclonal antibody R2 (Rønne et al, 1991, FEBS Lett. 288, pp 233ff) (mAb (R2)) (biotinylated) diluted 1:200. As above, the active blue beads were removed and the library recycled for a third screening by incubation with the target receptor, human urokinase plasminogen receptor (uPAR) diluted 1:200 and adding mAb (R2) diluted 1:500 and streptavidin alkaline phosphatase diluted 1:20,000 (Sigma 1 mg/ml). Active blue beads were isolated and analysed using a protein sequencer.

Based on the above screening six peptides interacting with uPAR were identified and surprisingly they all contained a β-cyclohexyl-L-alanine in the position neighbouring the L-phenylalanine.

Three of these peptides (AE100, dCha and AE 108) were synthesised as described in the section "Peptide synthesis", and the binding data for these peptides are shown in Table 2.

Thus, one of the high-affinity peptides found consisted of a 9-mer with the following sequence:

d Cha E s r Y L W S (dCha)

Subsequently it was found that changing the D-Asp to L-Asp i.e.

D Cha F s r Y L W S (AE105)

further improved binding. Clearly the peptide AE105 is a more interesting peptide than AE78, as it has a 48 fold slower off-rate.

The distance allowable between F and YLWS was studied by introduction of glycine (AE116) and β-alanine (AE 117) residues between D-arginine and L-tyrosine. It was found that the distance between F and YLWF in the discovered 9-mer was in fact critical for maintenance of high affinity human uPAR binding, since introduction of spacing residues abolished the binding (see Table 2).

The "Biacore Binding Assay"

Purified human suPAR (1 mg/ml in 50 mM phosphate, 150 mM NaCl, pH 7.4) was incubated with 5 µg/ml neuramimidase for 4 hours at 37° C.

In order to couple the neuramimidase-treated suPAR to a BIAcore sensor chip, 20 µg/ml suPAR in 10 mM sodium acetate (pH 5.0) was injected for 6 minutes at a flow rate of 5 µl per minute using a carboxymethylated dextran matrix (CM5 sensor chip), thereby immobilising approximately 1,500–2,000 resonance units (RU), which correspond to 1–2 ng suPAR/mm$^2$. The CM5 sensor chip was preactivated with N-hydroxysuccinimide/N-ethyl-N'-[3-(diethyl-amino)propyl]carbodiimide in accordance with the manufacturer's recommendations.

Surface plasmon resonance sensorgrams (RU versus time) were recorded at a flow rate of 10 µl per min at 5° C. using several different concentrations of the ligand (i.e. the relevant peptide or GFD) in the range from 10 to 1000 nM in running buffer (10 mM HEPES, 150 mM NaCl, 3 mM EDTA (pH 7.4) including 0.005% surfactant P-20).

The sensor chip was regenerated at the end of each run by injection of 0.1 M acetic acid, 0.5 M NaCl.

Data from parallel mock coupled flow cells (subjected to the coupling procedure in the presence of buffer only) served as blank sensorgrams for subtraction of changes in bulk refractive index.

The obtained sensorgrams were analysed by non-linear least squares fitting using BIAevaluation 2.0 software (Pharmacia Biosensor, Uppsala, Sweden) assuming single-site ssociation and dissociation models.

Example 4

Modification of the Identified β-Cyclohexyl-L-alanine-containing Sequence

Based on the above-mentioned sequences, a number of analogues were synthesised and tested (AE106, AE107, LCha, AE109, AE110, AE114, AE115, AE130, AE131, and AE132 see Table 2). These peptides had either activity of the same order of magnitude as AE105 or less than AE105.

Example 5

Construction of Peptomer Libraries

Synthesis of a peptidomimetic bead library comprising of a mixture of peptide-peptoid hybrids was accomplished by conventional peptoid chemistry using primary amines and bromacetic acid (Zuckerman et al 1992, Østergaard and Holm 1997). At variable positions in the constrained motif of the library, diversity was created by iterative divide, couple, and pool approach of the solid-phase bead support. The peptidomimetic library was constrained according to the following motif: D[L-Cha]FsrXXXX, where the lower case letters are D-amino acids, capital letters are L-amino acids, and X is selected randomly among the following 12 amino acids and 13 amines: L-Tyr, L-Trp, L-Leu, L-Cha, D-Try, D-Leu, D-Cha, D-Phe, D-His, β-naphthyl-L-alanine, $N_{im}$-benzyl-L-histidine, 1-aminoindane, tryptamine, diphenylethylamine, 1-aminonaphthaline, benzylamine, 2,3-dimethoxybenzylamine, 2-aminoethyl-2-pyridine, 2-(4-methoxy)-phenylethylamine, aminomethylcyclohexane, isobutylamine, 3,3-dimethylbutylamine, 1-butylamine and 2-methoxyethylamine. To reveal the chirality of a certain amino acid in a selected peptidomimetic during microsequencing, where both diastomers of that particular amino acid originally were present in the library, the L-amino acids were encoded with norleucine, whereas the corresponding D-amino acids were encoded with nor-valine.

The binding affinity of a number of analogues (AE124, AE125, AE126, AE128, AE129 Table 2) was tested and AE124, AE125, AE126 and AE128 showed dissociation constants in the same order of magnitude as the best of the peptides. Analogue AE126 showed a relative dissociation constant approximating those of AE105 and AE110.

Example 6

Dimeric Peptide with Higher Affinity

Having identified an optimised 9-mer peptide for human uPAR binding, it was considered relevant to investigate whether an even further increase in effectiveness could be achieved by making multimeric constructs which could bind to more than one uPAR molecule at the same time.

To test this hypothesis, two dimers were synthesised as described in the section entitled "Peptide Synthesis". In the first dimer constructed (AE118) one glycine residue was inserted at the C-terminus of AE105 and a single lysine residue was employed as the scaffold. The second dimer (AE120) differed from the AE118 dimer in that a beta-alanine was attached to the C-terminus glycine in the peptide sequence being linked to the α-amino group of the lysine scaffold. Thus, the structure of the two dimers were:

| | |
|---|---|
| [DChaFsrYLWSG]$_2$-K | (AE118) |
| α-[DChaFsrYLWSGβA]-ε-[DChaFsrYLWSG]-K | (AE120) |

The dimers AE118 and AE 120 both had a considerably slower off-rate (about 5–7 times slower) than the monomer (AE105) (see Table 2).

Example 7

Inhibition of uPA Binding to uPAR on the Surface of Human Carcinoma Cells

The peptides were tested for their ability to inhibit binding of radio-labelled amino terminal fragment (ATF) of human uPA to monolayer cultures of human MDA-MB-231 breast cancer cells.

Cell Binding Experiments with $^{125}$I-Labelled Human ATF

MDA-MB-231 BAG cells were harvested by trypsin/EDTA treatment and added to 5% FCS supplemented medium in 24 well cluster plates at a cell density of 100,000 cells per well or as indicated otherwise. For background estimation, wells without cells were included in order to measure binding of $^{125}$I-labelled ligand to the plastic. Next day the adherent monolayers were washed twice in binding-buffer (0.1% bovine serum albumin (BSA; Fraction V, Sigma) and 5 mM Hepes in Eagles MEM supplemented with Glutamax-1, pH 7.4). Before binding experiments, the cells were subjected to acid treatment to liberate receptor-bound endogenous uPA. Each culture well was incubated for 3 min at 23° C. with 200 µL of 0.05 M glycine-HCl, 0.1 M NaCl, pH 3.0, after which 200 µL of 0.5 M Hepes, 0.1 M NaCl pH 7.5 was added to neutralize the acid buffer. The wells were then emptied and washed once with binding buffer. Various competitors diluted in binding buffer were then added to the wells, followed by a pre-incubation at 37° C. for 15 min. Finally, $^{125}$I-labelled ligand was added to each well at a final concentration of 1 nM. Cells were incubated at 4° C. for 60 min, and then washed three times in binding-buffer. Subsequently, the cells were lysed by addition of 1 N NaOH to the wells. Aliquots from the wells were finally measured for radioactivity on a γ-counter. The results are shown in FIG. 3.

Results

Figure 3:
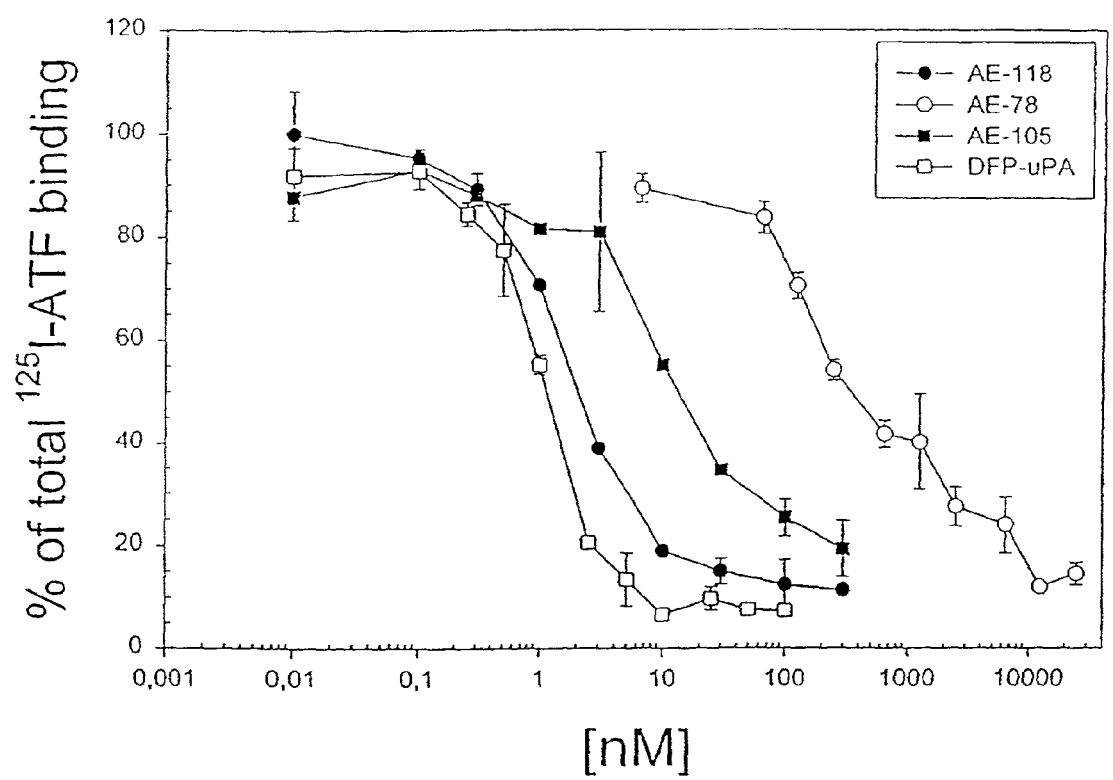
FIG. 3: Cell-binding assay.
The figure shows the effect of various peptide antagonists in the inhibition of the binding of ATF to monolayer cultures of human MDA-MB-231 breast cancer cells (Example 7).
Figure 4:
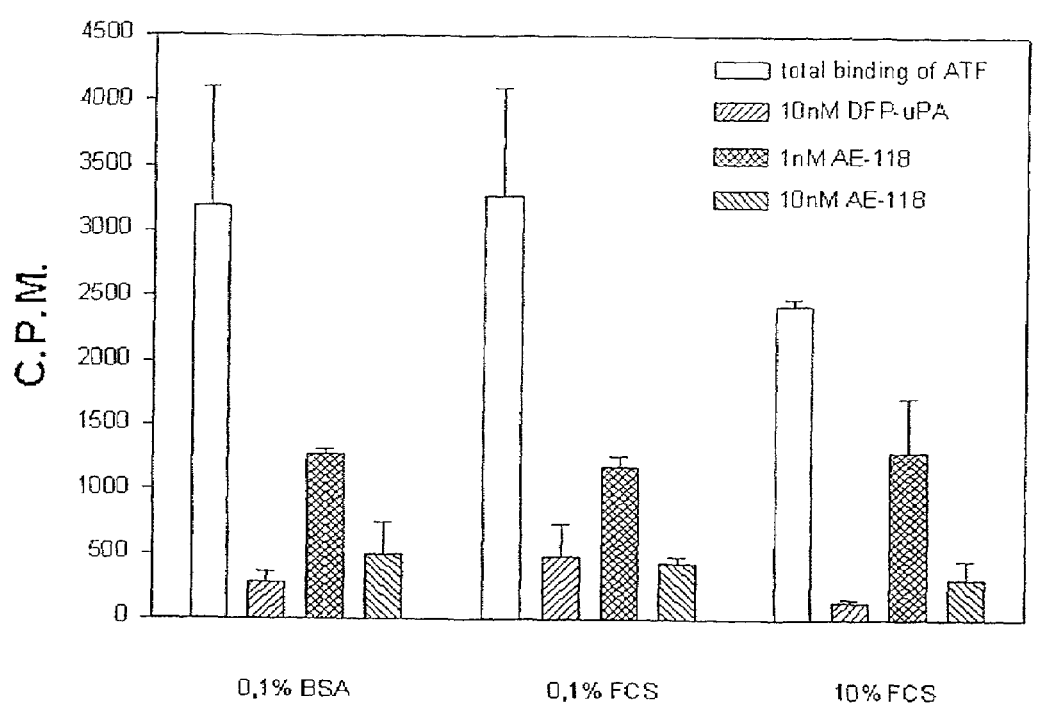
FIG. 4: Cell-binding assay.
The figure shows the effect of AE118 (1 and 10 nM, respectively as well as DFP-uPA (10 nM)) in the inhibition of the binding of ATF to monolayer cultures of human MDA-MB-231 breast cancer cells. The experiments were carried out in the presence of 0.1% bovine serum albumin, and 0.1% and 10% fetal calf serum, respectively (Example 7).

The results of cell-binding experiments are shown in FIGS. 3 & 4 and the numerical values are compiled in Table 3. The monomers AE105 and AE 120 were more effective than the reference peptide AE78 in inhibiting radio-labelled human ATF binding to human carcinoma cell-surface uPAR, and the dimer AE118 was considerably more effective than both, coming close to the potency of diisopropylfluorophosphate-inactivated human uPA (FIG. 3).

These cell binding experiments were done in the presence of 0.1% bovine serum albumin, but the effect of AE118 was also observed in the presence of 0.1% and even 10% fetal calf serum (FIG. 4). Thus the effect of AE118 on ligand binding to cell-surface uPAR can be maintained in the presence of a high background concentration of serum proteins, indicating favourable specificity for use in vivo (FIG. 4).

Example 8

Biological Stability of the Dimeric Peptides AE118 and AE120

The inclusion of D-amino acids (instead of the natural L-amino acids) results in a peptide product which has non-natural residues involved in peptide bonds, and these bonds are not likely to be hydrolysed by endopeptidases. Thus, dimeric peptides containing D-amino acids and a blocked C-terminus, like AE118 and AE120, are expected to have greater biological stability, due to resistance to enzymatic hydrolysis.

Peptide Stability in Mouse Serum Ex Vivo

Figure 5:
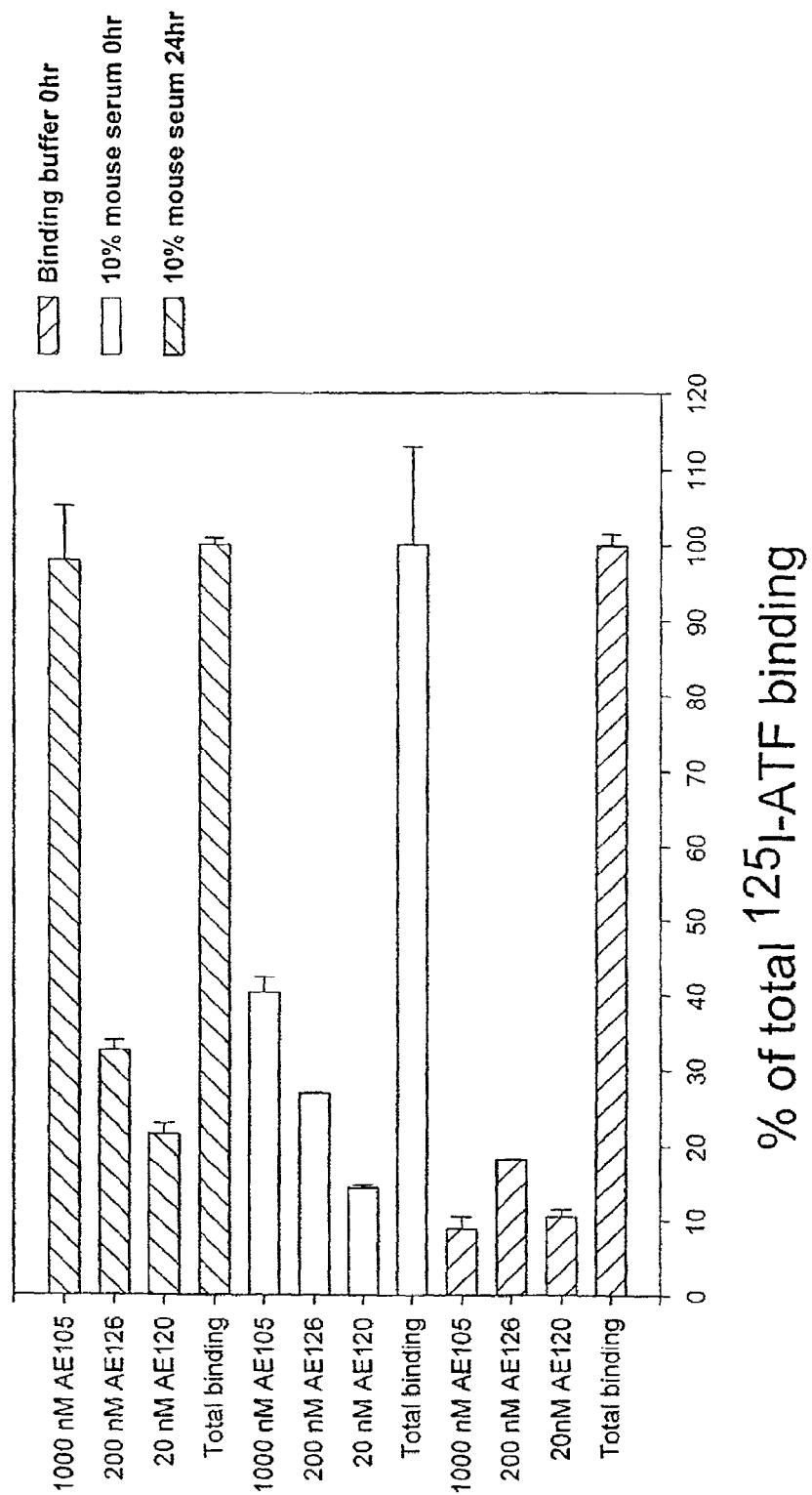
FIG. 5: Peptide stability in mouse serum.
Peptides were incubated with binding serum for 0 or 24 h and then tested in binding experiments with $^{125}$I-labelled human ATF. The figure shows results of the cell-binding experiments performed in Example 8.

Mouse blood was collected from anaesthetised mice (femal nu/nu-META/Bom (Bomholtgaard, Ry, Denmark)) by cardiac puncture. The blood samples were allowed to clot for 30 min at room temperature, followed by centrifugation at 1,000×g for 10 min at 20° C., and the sera were sterile filtered using 0.8 μm/0.2 μm filters (Acrodisc PF, Gelman Science, MI) and then stored at 4° C. until use. The peptide antagonists were added to fresh pooled mouse serum at the indicated concentrations (FIG. 5) and incubated at 37° C. for different periods, between 0 hours and 24 hours. Serum incubated samples were diluted 1:10 in binding buffer (0.1% bovine serum albumin and 5 mM Hepes in Eagles MEM supplemented with Glutamax-1, pH 7.4). Subsequently, cell binding experiments in the presence of $^{125}$I-labelled human ATF were performed in duplicates as above, by preincubating MDA-MB-231 BAG cells at 37° C. 15 min with the 1:10 diluted serum incubated samples ± peptides. In parallel, peptides diluted in binding buffer alone were included as controls.

AE118 and AE78 (for comparison) were incubated at 37° C. in the presence of 10% mouse serum for different time intervals, up to 24 hours. The incubation mixtures were tested for their ability to inhibit binding of radio-labelled human uPA amino terminal fragment (ATF) to monolayer cultures of human MDA-MB-231 breast cancer cells, as described in Example 7.

Figure 6:
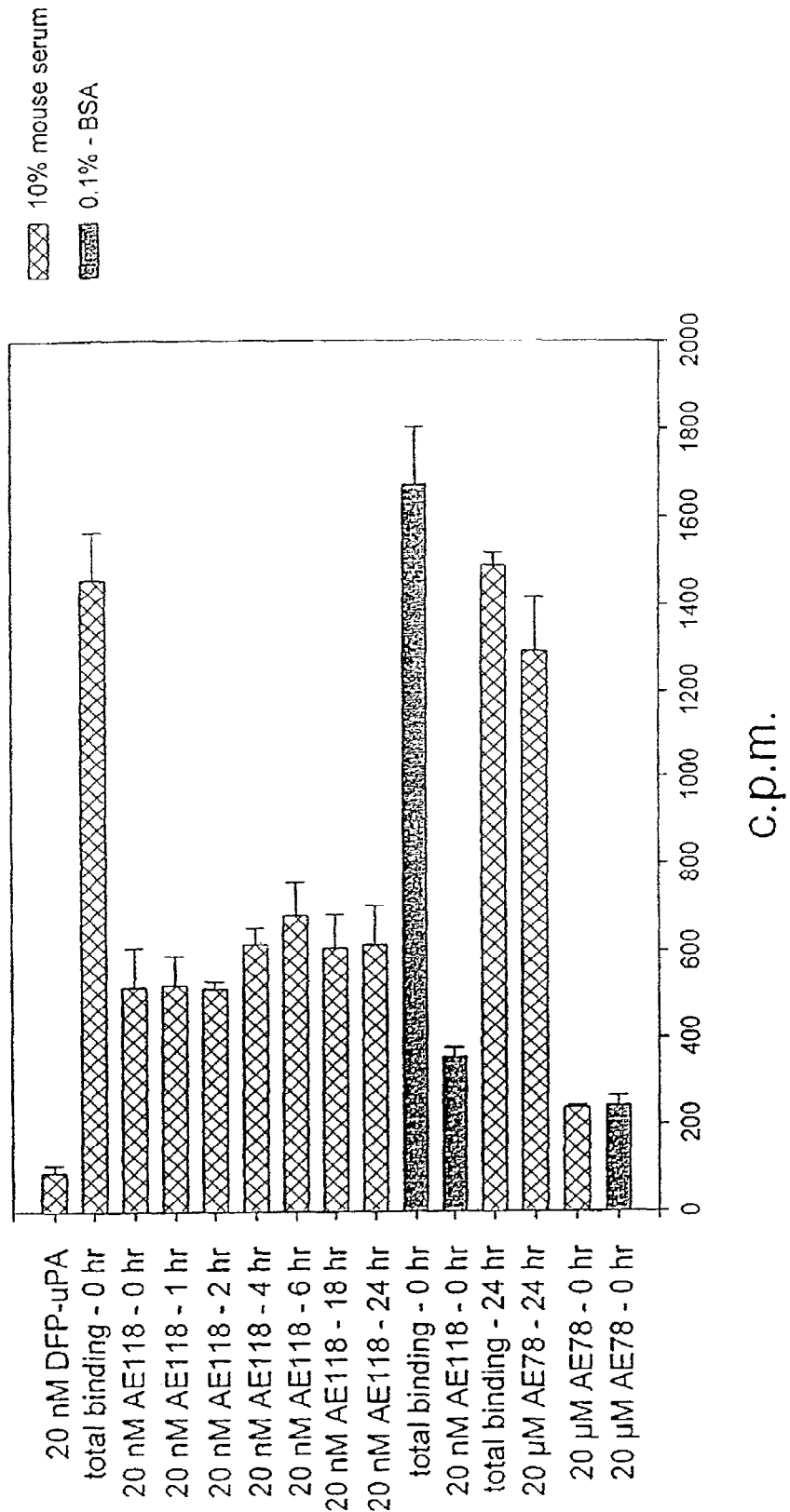
FIG. 6: Peptide stability in mouse serum.
Peptides were incubated for 0 to 24 h with buffer solution containing 0.1% BSA or pooled mouse serum and then tested in binding experiments with $^{125}$I-labelled human ATF. The figure shows the results of experiments performed in Example 8.

Incubation of AE118 with mouse serum for 24 h produced only a slight reduction in its ability to inhibit ATF binding to cells. On the contrary, AE78 lost the majority of its inhibitory activity after incubation for 24 h with mouse serum (FIG. 6).

Thus AE118 is clearly more resistant than AE78 to proteolytic degradation in a complex biological fluid.

Example 9

Pharmacokinetic Experiments-Presence of Peptides in Mouse Serum for a Prolonged Period Female nu/nu-META/Bom mice were injected intraperitoneally (i.p) with a solution of the peptide AE 120 (6.25 mg/ml in 0.5% (w/v) poloxamer 237 in PBS, pH 7.3) at a dose of 62.5 mg/kg mouse weight. At different time points between 1 hour and 24 hours, blood was collected from anaesthetised mice by cardiac puncture. The blood samples were allowed to clot for 30 min at room temperature, followed by centrifugation at 1,000×g for 10 min at 20° C., and the sera were stored frozen at −80° C. prior to assay. The presence of functional peptide antagonists in serum was determined by diluting the serum samples 1:10 with binding buffer (0.1% bovine serum albumin and 5 mM Hepes in Eagles MEM supplemented with Glutamax-1, pH 7.4) and analysing the samples in cell binding experiments with MDA-MB-231 BAG cells and $^{125}$I-labelled human ATF as described in Example 7. As an internal standard, AE120 was added exogenously to pooled mouse sera at final concentrations of 12.5 nM, 25 nM, 125 nM and 250 nM.

Figure 7:
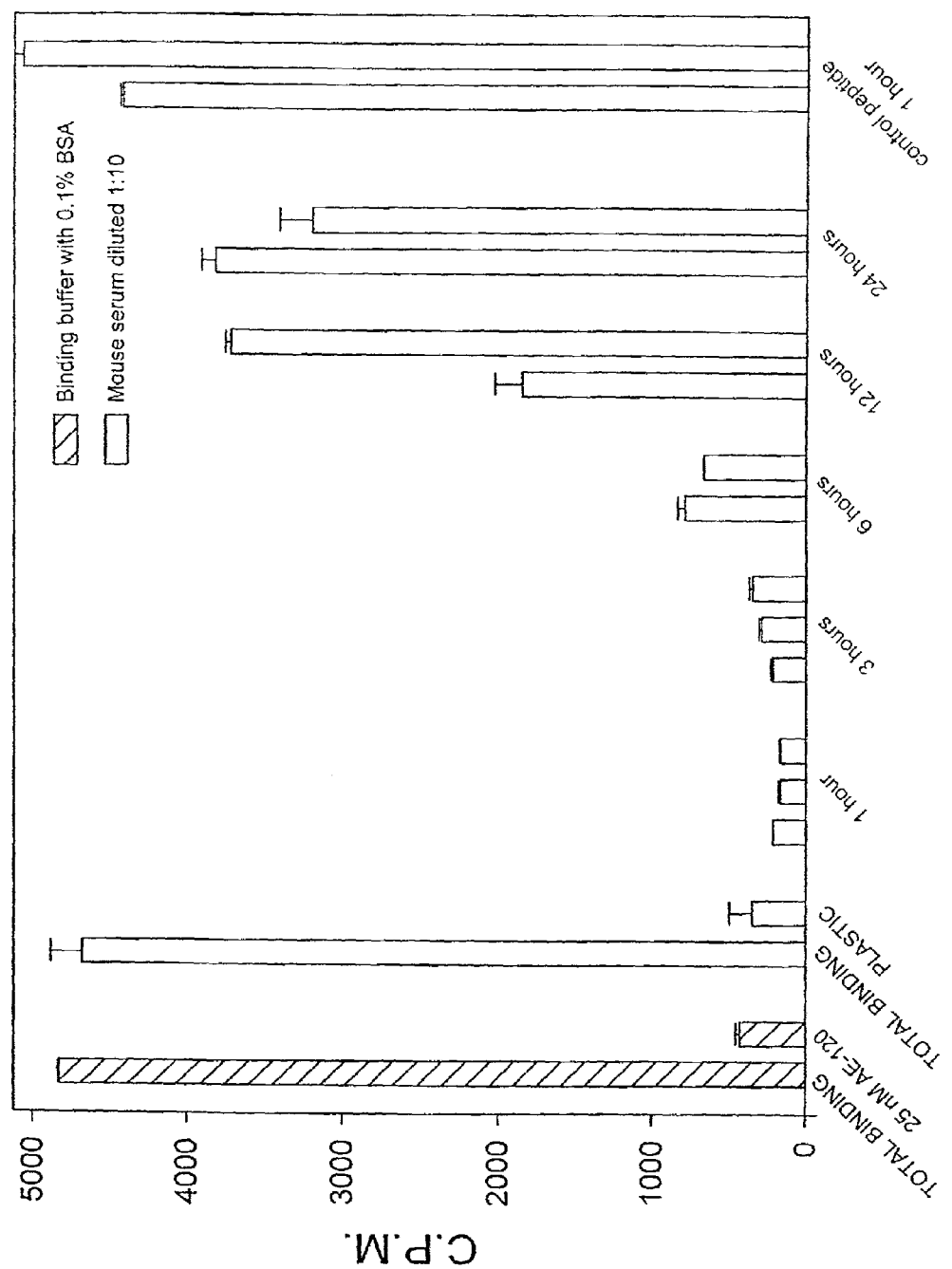
FIG. 7: Result of the pharmacokinetic experiment.
The figure shows the results of the experiments performed in Example 9.

The results (see FIG. 7) show that the peptide antagonist retained its activity in mouse serum for several hours. This result suggests that the peptide antagonists according to the present invention may be potential drugs in their own right, especially because of their low molecular weight and favourable solubility in aqueous media.

Example 10

Mouse Tolerance of Peptide Dosing

Mice were given a series of 4 intraperitoneal injections, spaced 8 hours apart, of peptide AE120 dispersed in a poloxamer formulation containing 2.9% DMSO. Each injection delivered 1.38 mg of peptide in 200 μL of formula, so that each mouse received a total of 5.52 mg over the 24-hour study period. Throughout the time of treatment there was no visible sign of any effect on the behaviour or well-being of the mice, so that the peptide at this dose was considered to be free of any significant toxicity.

Example 11

Species Specificity of the uPA Interaction with uPAR.

The species specificity of the interaction between the peptide antagonist AE120 and recombinant human versus mouse suPAR was measured by surface plasmon resonance in which the branched peptide antagonist AE120 was immobilised on the sensor chip via one of its two amino groups using traditional amine coupling chemistry. The binding of 200 nM purified human suPAR and mouse suPAR was measured in real times by recording the changes in the surface plasmon resonance. Human suPAR was found to bind with very high affinity, whereas purified mouse suPAR did not interact to any significant degree (FIG. 8).

Example 12

Figure 8:
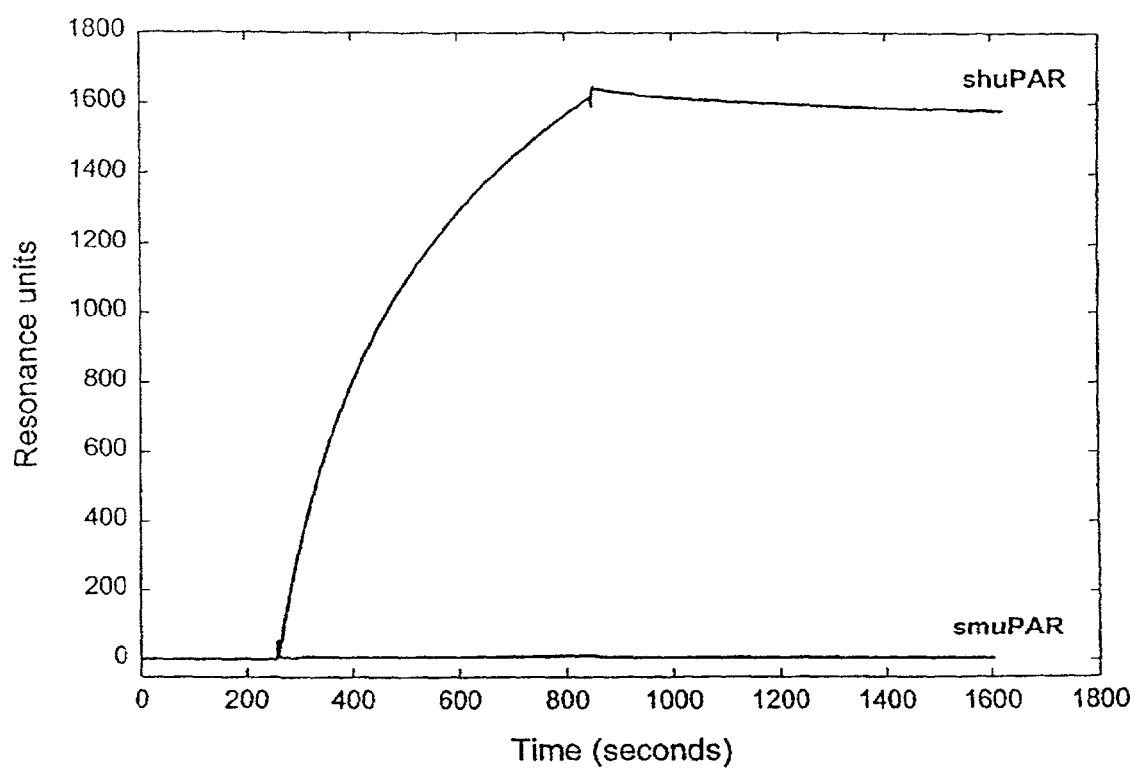
FIG. 8: Species specificity of uPAR interaction with immobilised peptide antagonist. Human and mouse suPARs were allowed to interact with AE120 in Biocore flow cells. The figure shows results of experiments performed in Example 11.

Sequence Comparison of the Relevant Amino Acids Subjected to Alanine Mutagenesis in Human uPAR to the Corresponding Residues of Hamster, Mouse, Rat and Bovine uPAR As shown in FIG. 8 we have demonstrated that the present peptide antagonists of the uPA-uPAR exhibit a very stringent species specificity, which then imposes limitations on which experimental animal model can be used to demonstrate the anti-metastatic and/or anti-invasive properties of the peptide antagonist. Any involvement of mouse stromal uPAR in human xenograft tumour invasion and metastasis performed in nude mice would therefore remain uninhibited during the treatment with AE120.

The functional epitope for antagonist binding was investigated by single site alanine scanning mutagenesis and revealed that $His^{249}$, $Asp^{254}$ and $Phe^{256}$ contribute by far the most to the free energy of binding. Among these, it was revealed that $His^{249}$ in human uPAR contributes most significantly to the free energy of antagonist binding, but not to the binding of the natural ligand (human uPA) and that only $His^{249}$ is changed when comparing the human sequence with the corresponding mouse and hamster sequence. Residues in human uPAR important for the free energy of human uPA binding are high-lighted in FIG. 9 by asterisks, whereas those important for binding of the peptide antagonist AE105 are boxed with a black frame. The residue in human uPAR, which is critical for antagonist binding and has been non-conservatively substituted in all other species ($His^{249}$), is marked with an arrow. Also shown is the ability of uPAR from different species to bind to human uPA and whether this binding can be inhibited by the peptide antagonist.

Based on these findings, we propose a method to circumvent the species-barrier by genetically engineering a mouse or hamster uPAR in such a way that the binding to the natural ligand uPA is unchanged but this binding is now rendered susceptible to inhibition by the peptide antagonists. One option to circumvent this species barrier would be to replace the mouse gene for uPAR by a mutated gene by gene targeting (Hanks et al 1995, Science 269, 679–682) in which $Gly^{272}$ has been changed to a His by the established "gene knock-out/gene knock-in" technology. In such a system we will possibly be able to study the inhibitory effect of the "species specific" peptide antagonists on mouse tumours.

It would therefore be possible to use a gene-targeted mouse as a model system for the intervention of cancer invasion and/or metastasis using the described "species specific" antagonists. Such a gene-targeted mouse would unlikely to have significantly altered endogenous function of uPAR; i.e. cells would probably bind mouse uPA, but it is possible that this binding would then be rendered susceptible to inhibition by the peptide antagonist. This would greatly help to demonstrate the efficacy of the antagonists in an experimental human tumour in mice.

Example 13

Dissociation Rate Constants for the Interaction Between an Immobilised Peptide Antagonist and VARIOUS suPAR Variants Carrying Single-Site Mutations.

Figure 10:
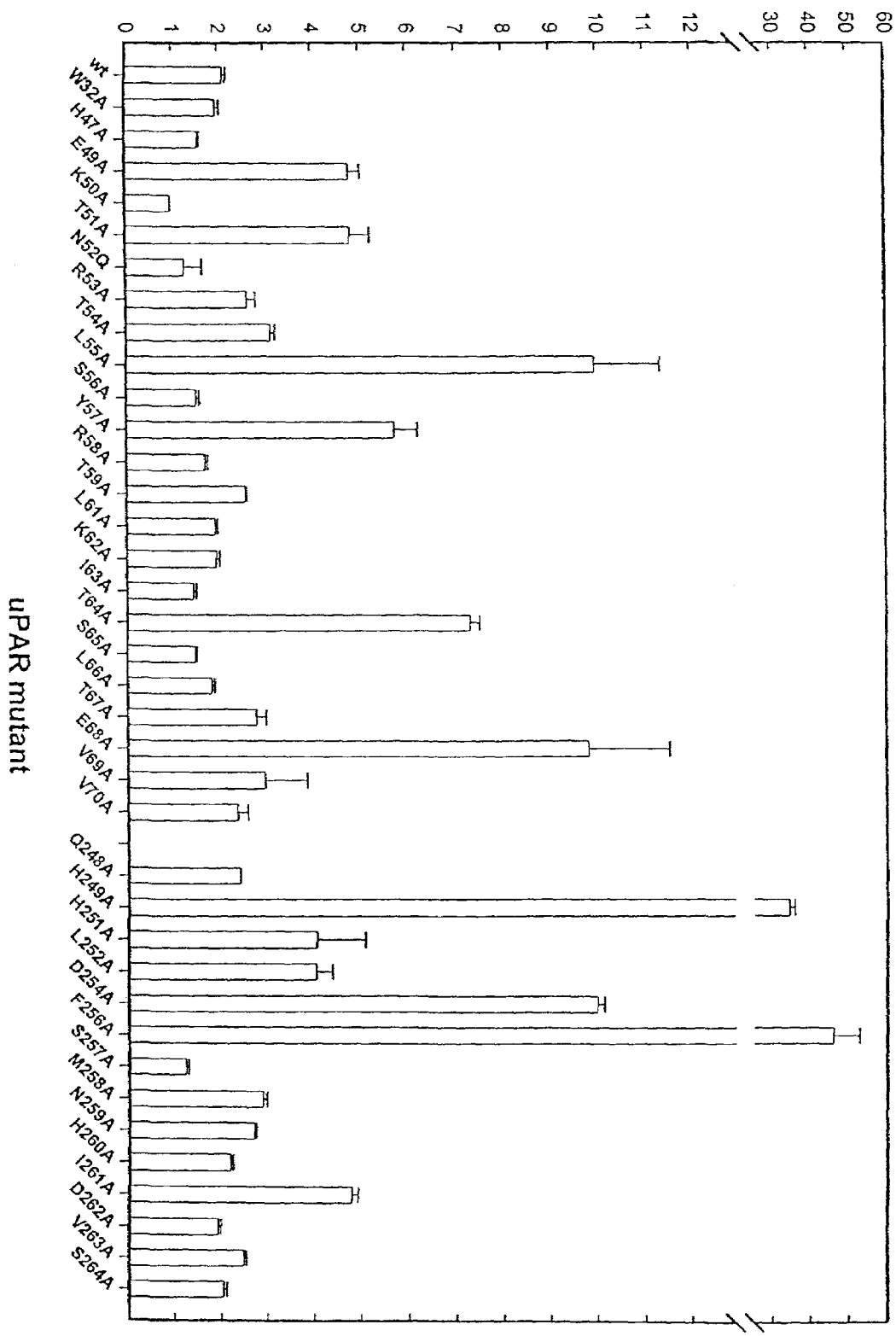
FIG. 10: Dissociation rate constants for the interacting between an immobilised peptide antagonist and various suPAR variants carrying single-site mutations.
The figure shows results of experiments performed in Example 13.

A linear derivative of the peptide antagonist AE105 having a 5 amino acid residue extension at the $NH_2$-terminus (KGSGGD-Cha-srYLWS) was immobilised via its $NH_2$ terminal lysine residue to the sensor chip by amine coupling chemistry. Binding of various purified single-site suPAR mutants was measured in real-time using surface plasmon resonance for 8 different concentrations in the range 200 nM to 2 nM. The mean of the dissociation rate constants along with its standard deviation are shown in FIG. 10 for each individual suPAR mutant.

TABLE 2

Summary of off-rates determined by Biacore technology for various peptides selected by combinatorial chemistry

| Code | Sequence | SEQ ID NO | $k_{diss}$ ($sec^{-1}$) | Relative $k_{diss}^{1)}$ |
|---|---|---|---|---|
| AE68[2] | SLNFSQYLWS | 1 | $12.9 \times 10^{-3}$ | 92.1 |
| dCha | d-Cha-F-s-r-Y-L-W-S | | $0.68 \times 10^{-3}$ | 4.9 |
| AE100 | e-Cha-F-s-y-Y-L-W-S | | $0.56 \times 10^{-3}$ | 4.0 |
| AE108 | t-Cha-F-s-r-Y-L-W-S | | $0.48 \times 10^{-3}$ | 3.4 |
| AE105 | D-cha-F-s-r-Y-L-W-S | | $0.21 \times 10^{-3}$ | 1.5 |
| AE116 | D-cha-F-s-r-G-Y-L-W-S | | no binding | >>100 |
| AE117 | D-cha-F-s-r-βA-Y-L-W-S | | no binding | >>100 |
| AE106 | D-Cha-F-S-r-Y-L-W-S | | $2.63 \times 10^{-3}$ | 18.7 |
| AE107 | d-Cha-F-S-r-Y-L-W-S | | $8.84 \times 10^{-3}$ | 63.1 |
| Lcha | S-L-Cha-F-s-Q-Y-L-W-S | | $3.49 \times 10^{-3}$ | 24.9 |
| AE109 | d-Cha-F-s-r-Y-$L^2$-nA-S | | $2.05 \times 10^{-3}$ | 14.6 |
| AE110 | D-Cha-F-s-R-Y-L-W-S | | $0.28 \times 10^{-3}$ | 2.0 |
| AE114 | D-Cha-F-s-r-Y-$L^1$-nA-S | | $0.59 \times 10^{-3}$ | 4.2 |
| AE115 | e-Cha-F-s-Y-Y-L-W-S | | $1.67 \times 10^{-3}$ | 11.9 |
| AE118 | [DChaFsrYLWSG]$_2$-K | | $0.04 \times 10^{-3}$ | 0.28 |
| AE120 | α-[DChaFsrYLWSGβA]-ε-[DChaFsrYLWSG]-K | | $0.03 \times 10^{-3}$ | 0.21 |
| AE130 | D-Cha-F-s-r-L-L-W-h | | $0.51 \times 10^{-3}$ | 3.6 |
| AE132 | D-Cha-F-s-r-Cha-L-W-l | | $0.53 \times 10^{-3}$ | 3.8 |
| AE131 | D-Cha-F-s-r-Y-L-Nal-h | | $0.56 \times 10^{-3}$ | 4.0 |
| AE78[3] | AEPMPHSLNFSQYLWYT | 2 | $10.1 \times 10^{-3}$ | 72.1 |
| AE104 | a-r-F-h-h-Y-L-W-S | | no binding | >>100 |
| AE111[4] | L-N-F-s-Q-Y-L-W-S | | $1.05 \times 10^{-3}$ | 7.5 |
| AE112 | D-F-F-s-r-Y-L-W-S | | $1.81 \times 10^{-3}$ | 12.9 |
| AE113 | D-N-F-s-r-Y-L-W-S | | no binding | >>100 |
| AE124 | D-Cha-F-s-r-DMB-f-TRA-MEA[5] | | $5.61 \times 10^{-3}$ | 40.0 |
| AE125 | D-Cha-F-s-r-DMLB-f-Bzl-MEA | | $0.74 \times 10^{-3}$ | 5.3 |

TABLE 2-continued

Summary of off-rates determined by Biacore technology for various peptides selected by combinatorial chemistry

| Code | Sequence | SEQ ID NO | $k_{diss}$ (sec$^{-1}$) | Relative $k_{diss}$[1]) |
|---|---|---|---|---|
| AE126 | D-Cha-F-s-r-DMB-f-AMN-MEA | | $0.37 \times 10^{-3}$ | 2.6 |
| AE128 | D-Cha-F-s-r-MEA-DMB-f-AMN | | no binding | >>100 |
| AE129 | D-Cha-F-s-r-DMB-f-DMB-l | | $0.54 \times 10^{-3}$ | 3.9 |
| pro-uPA | | | $0.10 \times 10^{-3}$ | 0.72 |
| ATF | | | $0.12 \times 10^{-3}$ | 0.86 |
| GFD | | | $0.14 \times 10^{-3}$ | 1.0 |

TABLE 3

Effect of various peptide antagonists in the inhibition of the binding of ATF to mono-layer cultures of human MDA-MB-231 breast cancer cells.

| Code | Sequence | SEQ ID NO | IC$_{50}$ (nM) |
|---|---|---|---|
| AE118 | [DChaFsrYLWSG]$_2$-K | | 2 |
| AE78 | AEPMPHSLNFSQYLWYT | 1 | 200 |
| AE105 | DchaFsrYLWS | | 10 |
| DFP-uPA | | | 1 |

What is claimed is:

1. A peptide comprising at least one peptide fragment of the general formula I:

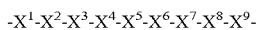  (I)

wherein $X^1$, $X^5$, $X^6$, $X^7$ and $X^9$ are independently selected from amino acids and $X^1$ is the N-terminal amino acid of the fragment and $X^9$ is the C-terminal amino acid of the fragment;

$X^2$ is selected from the group consisting of (a) amino acids of the general formula IIa

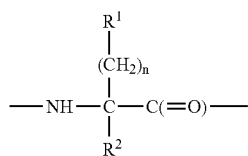  (IIa)

wherein n is an integer in the range from 0 to 3; $R^1$ is selected from the group consisting of optionally substituted five-, six- and seven-membered non-aromatic rings; $R^2$ is selected from the group consisting of hydrogen and $C_{1-4}$-alkyl; or, $R^1$ and $R^2$ together with the carbon atom to which they are bound form an optionally substituted cyclopentyl, cyclohexyl, cycloheptyl or decahydronaphthalenyl ring;

and (b) N-substituted amino acids of the general formula IIb

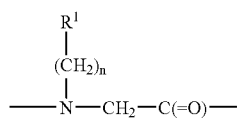  (IIb)

wherein n and $R^1$ are as defined above;

$X^3$ and $X^8$ are each independently selected from the group consisting of amino acids having hydrophobic side chains and amino acids having hydrophobic N-substituents;

$X^4$ is selected from the group consisting of (a) amino acids of the general formula IIIa

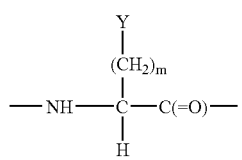  (IIIa)

wherein m is an integer in the range from 1 to 3, and Y is selected from the group consisting of OH, SH, $NH_2$, $CONH_2$, COOH and $OPO_3H$;

and (b) N-substituted amino acids of the general formula IIIb

  (IIIb)

wherein m and Y are as defined above.

2. A peptide according to claim 1, wherein $X^2$ is selected from L-amino acids of the general formula IIc

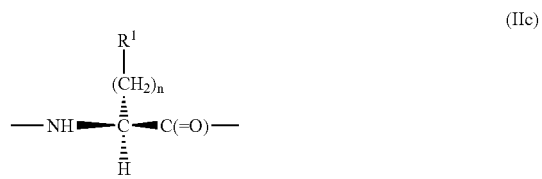  (IIc)

wherein n is 1 or 2 and $R_1$ is selected from the group consisting of optionally substituted five-, six- and seven-membered non-aromatic rings.

3. A peptide according to claim 1, wherein $X^3$ and $X^8$ are each independently selected from the group consisting of D- and L-phenylalanine, D- and L-tryptophan, D- and L-tyrosine, D- and L-histidine, β-2-naphthyl-L-alanine, β-2-naphthyl-D-alanine, β-1-naphthyl-L-alanine, β-1-naphthyl-D-indolylethyl)glycine, N-(2,3-dimethoxybenzyl)glycine, N-(3βethyl)glycine, N-benzylglycine, -(methylnaphthylyl)glycine, N-(2,2-diphenylethyl)glycine, -(indanyl)glycine, N-(2-ethyl-2-pyridinyl)glycine and N-(4-methoxyphenylethyl)glycine.

4. A peptide according to claim 1, which comprises more than one peptide fragment of the general formula I.

5. A peptide according to claim 4, wherein each of the peptide fragments are attached to a common scaffold.

6. A pharmaceutical composition comprising a peptide according to claim 1.

7. The peptide of claim 1 in which $X_2$ is Cha.

8. The peptide of claim 7 in which $X_3$ is L-Phe.

9. The peptide of claim 8 in which $X_1$ is D-Asp, L-Asp, D-Glu, L-Glu, D-Thr, L-Thr.

10. The peptide of claim 9 in which $X_1$ D-Asp or L-Asp.

11. The peptide of claim 10 in which $X_4$ D-Ser.

12. The peptide of claim 11 in which $X_5$ is L-Arg, D-Arg, L-Tyr, D-Tyr, L-Gln, or D-Gln.

13. The peptide of claim 12 in which $X_5$ is D-Arg.

14. The peptide of claim 13 in which $X_6$ to $X_9$ is (L-Tyr)-(L-Leu)-(L-Trp)-(L-Leu).

15. The peptide of claim 13 in which $X_6$ is DMB and $X_7$ is D-Phe.

16. The peptide of claim 13 in which $X_9$ is MEA.

17. A peptide according to claim 1, wherein n is 1.

18. A peptide according to claim 17 wherein $R^1$ is selected from the group consisting of cyclopentyl, cyclohexyl and cycloheptyl.

19. A peptide according to claim 18, wherein $R^1$ is cyclohexyl.

20. A peptide according to claim 1, wherein $X^2$ is selected from N-substituted amino acids of the general formula IIb, wherein n is 1 or 2.

21. A peptide according to claim 20, wherein n is 1.

22. A peptide according to claim 21 wherein $R^1$ is selected from the group consisting of cyclopentyl, cyclohexyl and cycloheptyl.

23. A peptide according to claim 22, wherein $R^1$ is cyclohexyl.

24. A peptide according to claim 1 wherein the hydrophobicity constant ($\pi$) of the side chain or the N-substituent of the amino acid in the $X^3$ position is at least 0.5.

25. A peptide according to claim 1 wherein the hydrophobicity constant ($\pi$) of the side chain or the N-substituent of the amino acid in the $X^8$ position is at least 0.5.

26. A peptide according to claim 1, wherein $X^3$ and $X^8$ are each independently selected from amino acids with aromatic side chains or aromatic N-substituents.

27. A peptide according to claim 26, wherein $X^3$ and $X^8$ are each independently selected from amino acids with aromatic side chains.

28. A peptide according to claim 3, wherein $X^3$ and $X^8$ are each independently selected from the group consisting of D- and L-phenylalanine, D- and L-tryptophan, D- and L-tyrosine, D- and L-histidine, β-2-naphthyl-L-alanine, β-2-naphthyl-D-alanine, β-1-naphthyl-L-alanine and β-1-naphthyl-D-analine.

29. A peptide according to claim 28, wherein $X^3$ is L-phenylalanine.

30. A peptide according to claim 1 where $X_3$ is selected from the group consisting of L-tryptophan, N-(2,3-dimethoxybenzyl)glycine, N-(3-indolylethyl)glycine, N-benzylglycine, N-(methylnaphthalyl)glycine, N-(2,2-diphenylethyl)glycine, N-(indanyl)glycine, N-(2-ethyl-2)pyridinyl)glycine and N-(4-methoxyphenylethyl)glycine.

31. A peptide according to claim 30, wherein $X^8$ is selected from the group consisting of L-tryptophan, N-benzylglycine, N-(methylnaphthalyl)glycine and N-(2,3-dimethoxybenzyl)glycine.

32. A peptide according to claim 1 wherein $X^4$ is selected from the group consisting of L-serine, D-serine, L-cysteine, D-cysteine, N-(hydroxymethyl)glycine and N-(methylthiol)glycine.

33. A peptide according to claim 32, wherein $X^4$ is selected from the group consisting of L-serine, D-serine, L-cysteine and D-cysteine.

34. A peptide according to claim 33, wherein $X^4$ is D-serine.

35. A peptide according to claim 1, wherein the peptide fragment is selected from the group consisting of
(D-Asp)-(β-cyclohexyl-L-alanine)-(Phe)-(D-Ser)-(D-Arg)-(Tyr)-(Leu)-(Trp)-(Ser),
(Ser)-(Leu)-(β-cyclohexyl-L-alanine)-(Phe)-(D-Ser)-(Gln)-(Tyr)(Leu)-(Trp)-(Ser),
(D-Glu)-(β-cyclohexyl-L-alanine)-(Phe)-(D-Ser)-(D-Tyr)-(Tyr)-(Leu)-(Trp)-(Ser),
(Asp)-(β-cyclohexyl-L-alanine)-(Phe)-(D-Ser)-(D-Arg)-(Tyr)-(Leu)-(Trp)-(Ser),
(Asp)-(β-cyclohexyl-L-alanine)-(Phe)-(Ser)-(D-Arg)-(Tyr)-Leu)-(Trp)-(Ser),
(D-Asp)-(β-cyclohexyl-L-alanine)-(Phe)-(Ser)-(D-Arg)-(Tyr)-Leu)-(Trp)-(Ser),
(D-Thr)-(β-cyclohexyl-L-alanine)-(Phe)-(D-Ser)-(D-Arg)-(Tyr)-(Leu)-(Trp)-(Ser),
(D-Asp)-(β-cyclohexyl-L-alanine)-(Phe)-(D-Ser)-(D-Arg)-(Tyr)-(Leu)-(β-2-naphthyl-L-alanine)-(Ser),
(Asp)-(β-cyclohexyl-L-alanine)-(Phe)-(D-Ser)-(Arg)-(Tyr)-(Leu)-(Trp)-(Ser),
(Asp)-(β-cyclohexyl-L-alanine)-(Phe)-(D-Ser)-(D-Arg)-(Tyr)-(Leu) (β-1-naphthyl-L-alanine)-(Ser),
(D-Glu)-(β-cyclohexyl-L-alanine)-(Phe)-(D-Ser)-(Tyr)-(Tyr)-(Leu)-(Trp)-(Ser),
(Asp)-(β-cyclohexyl-L-alanine)-(Phe)-(D-Ser)-(D-Arg)-(Leu)-(Leu)-(Trp)-(D-His),
(Asp)-(β-cyclohexyl-L-alanine)-(Phe)-(D-Ser)-(D-Arg)-(β-cyclohexyl-L-alanine)-(Leu)-(Trp)-(Ile),
(Asp)-(β-cyclohexyl-L-alanine)-(Phe)-(D-Ser)-(D-Arg)-(Tyr)-(Leu) (β-1-naphthyl-L-alanine)-(D-His),
(Asp)-(β-cyclohexyl-L-alanine)-(Phe)-(D-Ser)-(D-Arg)-(N-(2,3-dimethoxybenzyl)glycine)-(D-Phe)-(N-(3-indolylethyl)glycine)-(N-(2-methoxyethyl)glycine),
(Asp)-(β-cyclohexyl-L-alanine)-(Phe)-(D-Ser)-(D-Arg)-(N-(2,3-dimethoxybenzyl)glycine)-(D-Phe)-(N-benzylglycine)-(N-(2βthoxyethyl)glycine),
(Asp)-(β-cyclohexyl-L-alanine)-(Phe)-(D-Ser)-(D-Arg)-(N-(2,3-dimethoxybenzyl)glycine)-(D-Phe)-(N-(methylnaphthalyl)glycine)-(N-(2-methoxyethyl)glycine) and
(Asp)-(β-cyclohexyl-L-alanine)-(Phe)-(D-Ser)-(D-Arg)-(N-(2,3-dimethoxybenzyl)glycine)-(D-Phe)-(N-(2,3-dimethoxybenzyl)glycine)-(Ile).

* * * * *

UNITED STATES PATENT AND TRADEMARK OFFICE
CERTIFICATE OF CORRECTION

PATENT NO. : 7,026,282 B1  Page 1 of 1
APPLICATION NO. : 09/743329
DATED : April 11, 2006
INVENTOR(S) : Ploug et al.

It is certified that error appears in the above-identified patent and that said Letters Patent is hereby corrected as shown below:

Column 40, claim 3, line 31, "D-indolylethyl)glycine" should read --D-alanine--.

Column 40, claim 3, line 32, "N- (3βethyl)glycine" should read
--N- (3-indolylethyl) glycine--.

Column 41, claim 30, line 27, "$X_3$" should read --$X^8$--.

Column 42, claim 35, lines 12 and 14, "Leu)" should read -- (Leu) --.

Column 42, claim 35, line 36, "(N(2βthoxyethyl)" should read
-- (N- (2-methoxyethyl) --.

Column 40, claim 3, line 32, "- (methylnaphylyl)glycine" should read
--N- (methylnaphthalyl)glycine--.

Column 40, claim 3, line 33, "- (indanyl)glycine" should read --N- (indanyl)glycine--.

Signed and Sealed this

Tenth Day of April, 2007

JON W. DUDAS
*Director of the United States Patent and Trademark Office*

SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: AE68

<400> SEQUENCE: 1

Ser Leu Asn Phe Ser Gln Tyr Leu Trp Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: AE78

<400> SEQUENCE: 2

Ala Glu Pro Met Pro His Ser Leu Asn Phe Ser Gln Tyr Leu Trp Tyr
1               5                   10                  15

Thr

<210> SEQ ID NO 3
<211> LENGTH: 37
<212> TYPE: PRT
<213> ORGANISM: Homo sapiens

<400> SEQUENCE: 3

```
Trp His Glu Lys Thr Asn Arg Thr Leu Ser Tyr Arg Thr Leu Lys Ile
1               5                   10                  15

Thr Ser Leu Thr Glu Val Val Gln His His Leu Asp Phe Ser Met Asn
            20                  25                  30

His Ile Asp Val Ser
            35

<210> SEQ ID NO 4
<211> LENGTH: 37
<212> TYPE: PRT
<213> ORGANISM: Cricetus cricetus

<400> SEQUENCE: 4

Trp His Glu Lys Thr Asn Arg Thr Met Ser Tyr Arg Val Ser Lys Ile
1               5                   10                  15

Ile Ser Leu Ala Glu Val Val Gln Gly His Val Asp Phe Leu Leu Ser
            20                  25                  30

His Pro Asn Ile Ser
            35

<210> SEQ ID NO 5
<211> LENGTH: 37
<212> TYPE: PRT
<213> ORGANISM: Mus musculus

<400> SEQUENCE: 5

Trp His Glu Lys Thr Asn Arg Thr Met Ser Tyr Arg Met Ser Met Ile
1               5                   10                  15

Ile Ser Leu Thr Glu Thr Val Gln Gly His Val Asp Phe Pro Thr His
            20                  25                  30

Asn Val Ser Val Ser
            35

<210> SEQ ID NO 6
<211> LENGTH: 37
<212> TYPE: PRT
<213> ORGANISM: Rattus norvegicus

<400> SEQUENCE: 6

Trp His Glu Lys Thr Asn Arg Thr Met Ser Tyr Arg Met Ser Val Ile
1               5                   10                  15

Val Ser Leu Thr Glu Thr Val Gln Gly His Val Asp Phe Gln Thr His
            20                  25                  30

Asn Leu Ser Thr Ser
            35

<210> SEQ ID NO 7
<211> LENGTH: 37
<212> TYPE: PRT
<213> ORGANISM: Bos taurus

<400> SEQUENCE: 7

Trp His Asp Lys Thr Asn Arg Ser Met Ser Tyr Arg Ala Asp Gln Ile
1               5                   10                  15

Ile Thr Leu Ser Glu Thr Val Gln Ser His Val Glu Phe Asp Leu Thr
            20                  25                  30

His Val Asn Val Ser
            35
```